(12) United States Patent
Gallagher et al.

(10) Patent No.: US 6,335,340 B1
(45) Date of Patent: Jan. 1, 2002

(54) COMPOUNDS OF HETEROARYL SUBSTITUTED IMIDAZOLE, THEIR PHARMACEUTICAL COMPOSITONS AND USES

(75) Inventors: Timothy Francis Gallagher, Harleysville; Jeffrey Charles Boehm, King of Prussia; Jerry Leroy Adams, Wayne, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/581,842

(22) PCT Filed: Dec. 17, 1998

(86) PCT No.: PCT/US98/26862

§ 371 Date: Jun. 16, 2000

§ 102(e) Date: Jun. 16, 2000

(87) PCT Pub. No.: WO99/32121

PCT Pub. Date: Jul. 1, 1999

Related U.S. Application Data

(60) Provisional application No. 60/068,393, filed on Dec. 19, 1997.

(51) Int. Cl.[7] ................. A01N 43/58; A61K 31/50; C07D 401/00; C07D 403/00; C07D 403/02
(52) U.S. Cl. ............. 514/252.05; 514/275; 514/397; 544/238; 544/331; 548/314.7
(58) Field of Search ................. 514/252.05, 275, 514/397; 544/331, 238; 548/314.7

(56) References Cited

U.S. PATENT DOCUMENTS

| | | | |
|---|---|---|---|
| 5,593,992 A | 1/1997 | Adams et al. | 514/235.8 |
| 5,658,903 A | 8/1997 | Adams et al. | 514/235.8 |
| 5,663,334 A | 9/1997 | Sheldrake et al. | 544/122 |
| 5,670,527 A | 9/1997 | Adams et al. | 514/341 |
| 5,739,143 A | 4/1998 | Adams et al. | 514/275 |
| 5,859,041 A | 1/1999 | Liverton et al. | 514/396 |

Primary Examiner—Mukund J. Shah
Assistant Examiner—Tamthom N Truong
(74) Attorney, Agent, or Firm—Dara L. Dinner; Stephen Venetianer; Charles M. Kinzig

(57) ABSTRACT

Compounds of 1,4,5-substituted imidazole wherein one of the substituents can be a substituted pyrimidine, pyridazine or 1,2,4-triazine. These compounds and their pharmaceutical compositions are used in treating cytokine mediated diseases by inhibiting the production of IL-1 (interleukin-1), IL-8 (interleukin-8), and TNF (tumor necrosis factor).

7 Claims, 2 Drawing Sheets

Figure 1:
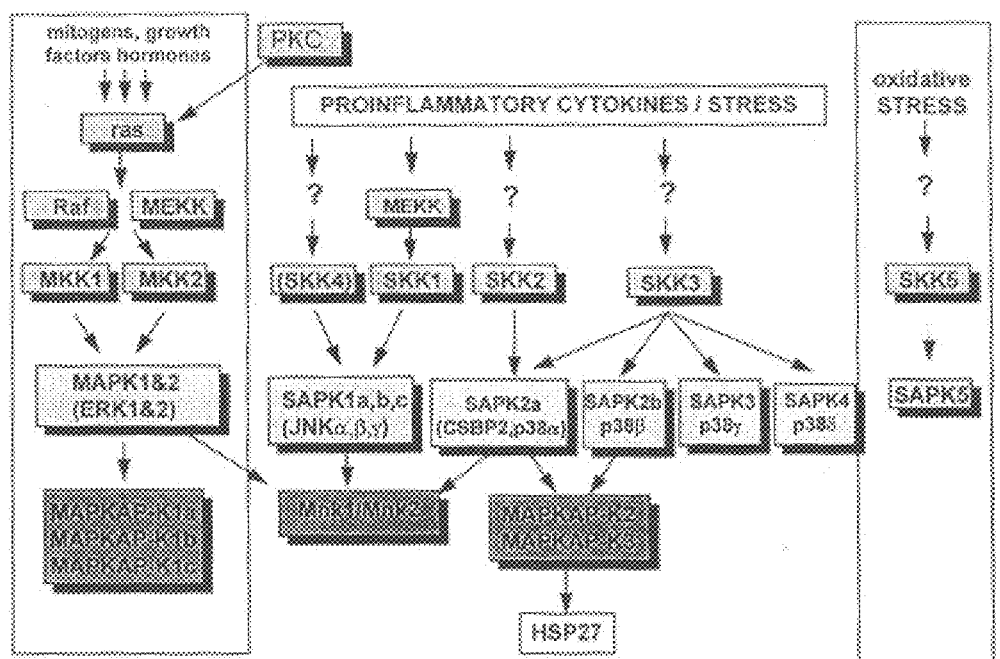

COMPOUNDS OF HETEROARYL SUBSTITUTED IMIDAZOLE, THEIR PHARMACEUTICAL COMPOSITONS AND USES

RELATED APPLICATIONS

This is a 371 of International Application PCT/US98/26862, filed Dec. 17, 1998, which claims benefit from the following Provisional Applications, No. 60/068,393, filed Dec. 19, 1997.

This application claims the benefit of provisional application No. 60/068,393 filed Dec. 19, 1997.

FIELD OF THE INVENTION

This invention relates to a novel group of imidazole compounds, processes for the preparation thereof, the use thereof in treating cytokine mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phopholipases are the essential machinery by which the signal is further transmitted within the cell [Marshall, J. C. Cell, 80, 179–278 (1995)]. Protein kinases can be categorized into five classes with the two major classes being, tyrosine kinases and serine/threonine kinases depending upon whether the enzyme phosphorylates its substrate(s) on specific tyrosine (s) or serine/threonine(s) residues [Hunter, T., *Methods in Enzymology* (*Protein Kinase Classification*) p. 3, Hunter, T.; Sefton, B. M.; eds. vol. 200, Academic Press; San Diego, 1991].

For most biological responses, multiple intracellular kinases are involved and an individual kinase can be involved in more than one signaling event. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. Cell, 80, 179 (1995); Herskowitz, I. Cell, 80, 187 (1995); Hunter, T. Cell, 80, 225 (1995);Seger, R., and Krebs, E. G. FASEB J., 726–735 (1995)].

While many signaling pathways are part of cell homeostasis, numerous cytokines (e.g., IL-1 and TNF) and certain other mediators of inflammation (e.g., COX-2, and iNOS) are produced only as a response to stress signals such as bacterial lipopolysaccharide (LPS). The first indications suggesting that the signal transduction pathway leading to LPS-induced cytokine biosynthesis involved protein kinases came from studies of Weinstein [Weinstein, et al., *J. Immunol.* 151, 3829(1993)] but the specific protein kinases involved were not identified. Working from a similar perspective, Han [Han, et al., *Science* 265, 808(1994)] identified murine p38 as a kinase which is tyrosine phosphorylated in response to LPS. Definitive proof of the involvement of the p38 kinase in LPS-stimulated signal transduction pathway leading to the initiation of proinflammatory cytokine biosynthesis was provided by the independent discovery of p38 kinase by Lee [Lee; et al., *Nature*, 372, 739(1994)] as the molecular target for a novel class of anti-inflammatory agents. The discovery of p38 (termed by Lee as CSBP 1 and 2) provided a mechanism of action of a class of anti-inflammatory compounds for which SK&F 86002 was the prototypic example. These compounds inhibited IL-1 and TNF synthesis in human monocytes at concentrations in the low uM range [Lee, et al., *Int. J. Immunopharmac.* 10(7), 835(1988)) and exhibited activity in animal models which are refractory to cyclooxygenase inhibitors [Lee; et al., *Annals N. Y. Acad. Sci.*, 696, 149 (1993)].

Figure 2:
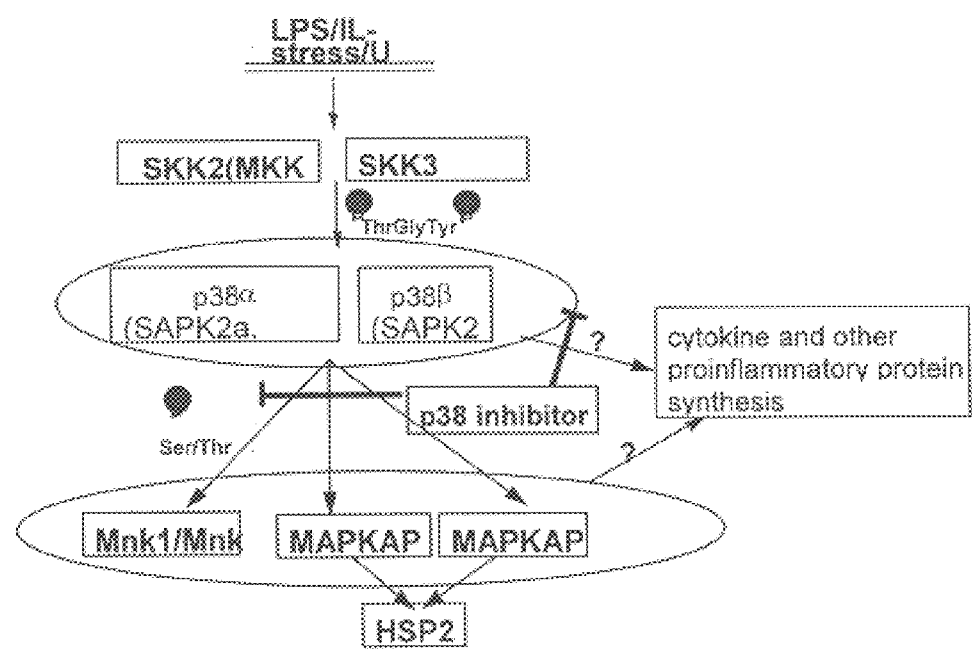

It is now firmly established that CSBP/p38 is a one of several kinases involved in a stress-response signal transduction pathway which is parallel to and largely independent of the analogous mitogen-activated protein kinase (MAP) kinase cascade (FIG. 1). Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27 (FIG. 2). It is not yet known whether MAPKAP-2, MAPKAP-3, Mnk1 or Mnk2 are involved in cytokine biosynthesis or alternatively that inhibitors of CSBP/p38 kinase might regulate cytokine biosynthesis by blocking a yet unidentified substrate downstream from CSBP/p38 [Cohen, P. *Trends Cell Biol.*, 353–361(1997)].

What is known, however, is that in addition to inhibiting IL-1 and TNF, CSBP/p38 kinase inhibitors (SK&F 86002 and SB 203580) also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that CSBP/p38 is involved not only cytokine synthesis, but also in cytokine signaling [CSBP/P38 kinase reviewed in Cohen, P. *Trends Cell Biol.*, 353–361(1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells [review of the biological activities which have been attributed to IL-1 Dinarello, *J. Clinical Immunology*, 5 (5), 287–297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera.* 279 (3): 1453–1461.(1996); Griswold, et al, *Pharmacol. Comm.* 7, 323–229 (1996)].

There remains a need for treatment, in this field, for compounds which are cytokine suppressive anti-inflammatory drugs, i.e. compounds which are capable of inhibiting the CSBP/p38/RK kinase.

SUMMARY OF THE INVENTION

This invention relates to the novel compounds of Formula (I) and pharmaceutical compositions comprising a compound of Formula (I) and a pharmaceutically acceptable diluent or carrier.

Another aspect of the present invention relates to a method of treating a CSBP/RK/p38 kinase mediated disease, in a mammal in need thereof which comprises administering to said mammal an effective amount of a compound of Formula (I).

This invention also relates to a method of inhibiting cytokines and the treatment of a cytokine mediated disease, in a mammal in need thereof which comprises administering to said mammal an effective amount of a compound of Formula (I).

This invention more specifically relates to a method of inhibiting the production of IL-1 in a mammal in need thereof which comprises administering to said mammal an effective amount of a compound of Formula (I).

This invention more specifically relates to a method of inhibiting the production of IL-8 in a mammal in need thereof which comprises administering to said mammal an effective amount of a compound of Formula (I).

This invention more specifically relates to a method of inhibiting the production of TNF in a mammal in need thereof which comprises administering to said mammal an effective amount of a compound of Formula (I).

Accordingly, the present invention provides for compound of Formula (I):

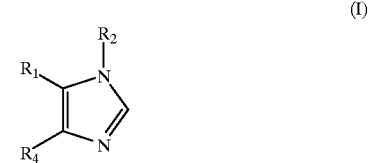

(I)

$R_1$ is 4-pyridazinyl, or a 1,2,4-triazin-5-yl ring, which ring is substituted with $NHR_a$ and optionally substituted with an additional, independent, substituent of $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_b$, or $NHR_a$;

$R_a$ is aryl, aryl$C_{1-6}$alkyl, heterocyclic, heterocyclyl$C_{1-6}$ alkyl, heteroaryl, heteroaryl$C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_3$, halo-substituted-$C_{1-4}$ alkyl, $C_{1-4}$ alkyl, $(CR_{10}R_{20})_{m''}NR_{10}C(Z)R_3$, $NR_{10}S(O)_{m'}R_8$, $NR_{10}S(O)_{m'}NR_7R_{17}$, $ZC(Z)R_3$ or $(CR_{10}R_{20})_{m''}NR_{13}R_{14}$;

v is 0, or an integer having a value of 1 or 2;

m is 0, or the integer 1 or 2;

m' is an integer having a value of 1 or 2, m" is 0, or an integer having a value of 1 to 5;

$R_2$ is —$(CR_{10}R_{20})_nOR_9$, heterocyclyl, heterocyclyl$C_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$cycloalkenyl-$C_{1-10}$-alkyl, aryl, aryl$C_{1-10}$alkyl, heteroaryl, heteroaryl-$C_{1-10}$-alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}OR_{20})_nNR_{13}R_{14}$, $(CR_{10}R_{20})_nNO_2$, $(CR_{10}R_{20})_nCN$, $(CR_{10}R_{20})_nSO_2R_{18}$, $(CR_{10}OR_{20})_nS(O)_m NR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-$R_{18}$)-1,2,4-oxadizaol-3-yl or 4-($R_{12}$)-5-($R_{18}R_{19}$)-4,5-dihydro-1,2,4-oxadiazol-3-yl; wherein the aryl, arylalkyl, heteroaryl, heteroaryl alkyl, cycloalkyl, cycloalkyl alkyl, heterocyclic and heterocyclic alkyl groups may be optionally substituted;

n is an integer having a value of 1 to 10;

n' is 0, or an integer having a value of 1 to 10;

Z is oxygen or sulfur;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties —$SR_5$ being —$SNR_7R_{17}$ and —$SOR_5$ being —SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$_{1-4}$alkyl, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})NR_{13}R_{14}$; wherein the aryl, arylalkyl, heteroaryl, heteroaryl alkyl may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached forn a heterocyclic ring of 5 to 7 members which ring optionally contains an additional heteroatom selected from oxygen, sulfur or $NR_9$;

$R_{15}$ is $R_{10}$ or $C(Z)$—$C_{1-4}$ alkyl;

$R_{16}$ is $C_{1-10}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$_{1-10}$alkyl, heterocyclyl, heterocyclyl-$C_{1-10}$alkyl, heteroaryl or heteroaryl$_{1-10}$alkyl;

$R_{19}$ is hydrogen, cyano, $C_{1-4}$ alkyl, $C_{3-7}$ cyloalkyl or aryl; or a pharmaceutically acceptable salt thereof This invention also relates to a novel synthesis for compounds of Formula (A), as described herein by solid phase synthesis.

This invention also relates to novel compounds, pharmaceutical compositions thereof, and their use in the treatment of CSBP/RK/p38 kinase mediated diseases, in a mammal in need thereof.

DETAILED DESCRIPTION OF THE DRAWINGS

FIG. 1 demonstrates the mitogen-activated protein kinase (MAP) kinase cascade.

FIG. 2 demonstrates the p38 kinase pathway.

DETAILED DESCRIPTION OF THE INVENTION

In Formula (I), suitable $R_1$ moieties a 4-pyridazinyl, 1,2,4-triazin-5-yl ring. The $R_1$ moiety is substituted with $NHR_a$, wherein $R_a$ is aryl, aryl$C_{1-6}$alkyl, heterocyclic, heterocyclic $C_{1-6}$ alky, heteroaryl, or heteroaryl $C_{1-6}$alkyl; and wherein each of these moieties may be optionally substituted.

When $R_a$ is aryl, it is preferably phenyl or naphthyl. When $R_a$ is aryl alkyl, it is preferably benzyl or napthylmethyl. When $R_a$ is heterocyclic or heterocyclic alkyl moiety the heterocycle is preferably pyrrolindinyl, piperidine, morpholino, tetrahydropyran, tetrahydrothiopyranyl, tetrahydrothiopyransulfinyl, tetrahydrothiopyransulfonyl, pyrrolindinyl, or piperonyl, more preferably piperidine.

When $R_a$ is a heteroaryl or heteroaryl alyl, it is heteroaryl is preferably imnidazole, indole, pyrrole, pyrazole, furan, thiophene, quinoline, isoquinoline, quinazolinyl, pyridine, pyrimidine, oxazole, thiazole, thiadiazole, triazole, or benzimidazole, more preferably imidazole, or indole.

As noted above, the aryl, heterocyclic and heteroaryl rings may be optionally substituted, one or more times, preferably 1 to 3 times, independently, by halogen; $C_{1-4}$ alkyl, such as methyl, ethyl, propyl, isopropyl, or t-butyl; halosubstituted $C_{1-4}$ alkyl, such as $CF_3$; hydroxy; hydroxy substituted $C_{1-4}$ alkyl; $C_{1-4}$ alkoxy, such as methoxy or ethoxy; halosubstituted $C_{1-4}$ alkoxy, such as $OCF_2CF_2H$ or $OCF_3$; $S(O)_m$alkyl and $S(O)m$ aryl (wherein m is 0, 1, or 2); $C(O)OR_{11}$, such as $C(O)C_{1-4}$ alkyl or $C(O)OH$ moieties; $C(O)R_{11}$; $OC(O)R_{18}$, wherein the $R_{18}$ moiety may be optionally substituted as herein described below; O—$(CH_2)s$—O—, such as in a ketal or dioxyalkylene bridge and s is an integer of 1 to 3; amino; mono- and di-$C_{1-6}$ alkyl substituted amino; $N(R_{10})C(O)R_b$; an N-heterocyclyl ring which ring has from 5 to 7 members and optionally contains an additional heteroatom selected from oxygen, sulfur or $NR_{15}$; optionally substituted aryl, such as phenyl; or an optionally substituted aryl $C_{1-4}$ alkyl, such as benzyl or phenethyl.

Suitably, in compounds of Formula (I), $R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl.

Suitable $R_a$ groups include, benzyl, halosubstituted benzyl, napthylmethyl, phenyl, halosubstituted phenyl, morpholinopropyl, imidazole propyl, ethyl-1-piperidinecarboxylate, piperonyl, piperidin-4-yl, alkyl substituted piperidine, such as 1-methyl piperidine, or 2,2,6,6-tetramethylpiperidin-4-yl, chlorotryptamine, tetrahydrothiopyranyl, ethyl-N—C(O)O t-butyl, propylethoxy, 2-aminoethyl, propylimidazole.

It is recognized that the $R_1$ group may additionally be substituted by $C_{1-4}$ alkyl, halo, OH, $C_{1-4}$ alkoxy, $C_{1-4}$ alkylthio, $C_{1-4}$ alkylsulfinyl, $CH_2OR_{12}$, amino, mono- and di-$C_{1-6}$ alkylsubstituted amino, $N(R_{10})C(O)R_b$, $NHR_a$ or an N-heterocyclyl ring which ring has from 5 to 7 members and optionally contains an additional heteroatom selected from oxygen, sulfur or $NR_{15}$. Suitably, when the additional group is other than a dialkylsubstituted amino.

When the additional $R_1$ optional substituent is $N(R_{10})C(O) R_b$, $R_b$ is preferably $C_{1-6}$ alkyl; preferably $R_{10}$ is hydrogen. It is also recognized that the $R_b$ moieties, in particular the $C_{1-6}$ alkyl group may be optionally substituted, preferably from one to three times, preferably with halogen, such as fluorine, as in trifluoromethyl or trifluoroethyl.

Suitably, $R_4$ is phenyl, napth-1-yl or naphth-2-yl, or a heteroaryl, which is optionally substituted by one or two substituents. More preferably $R_4$ is a phenyl or naphthyl ring. Suitable substitutions for $R_4$ when this is a 4-phenyl, 4-naphth-1-yl, 5-naphth-2-yl or 6-naphth-2-yl moiety are one or two substituents each of which are independently selected from halogen, $SR_5$, $SOR_5$, $OR_{12}$, $CF_3$, or $(CR_{10}R_{20})_vNR_{10}R_{20}$, and for other positions of substitution on these rings preferred substitution is halogen, $S(O)_mR_3$, $OR_3$, $CF_3$, $(CR_{10}R_{20})_{m''}NR_{13}R_{14}$, $NR_{10}C(Z)R_3$ and $NR_{10}S(O)_mR_8$. Preferred substituents for the 4-position in phenyl and naphth-1-yl and on the 5-position in naphth-2-yl include halogen, especially fluoro and chloro and —$SR_5$ and —$SOR_5$ wherein $R_5$ is preferably a $C_{1-2}$ alkyl, more preferably methyl; of which the fluoro and chloro is more preferred, and most especially preferred is fluoro. Preferred substituents for the 3-position in phenyl and naphth-1-yl rings include: halogen, especially fluoro and chloro; $OR_3$, especially $C_{1-4}$ alkoxy; $CF_3$, $NR_{10}R_{20}$, such as amino; $NR_{10}C(Z)R_3$, especially $NHCO(C_{1-10}$ alkyl); $NR_{10}S(O)_mR_8$, especially $NHSO_2(C_{1-10}$ alkyl), and $SR_3$ and $SOR_3$ wherein $R_3$ is preferably a $C_{1-2}$ alkyl, more preferably methyl. When the phenyl ring is disubstituted preferably it is two independent halogen moieties, such as fluoro and chloro, preferably di-chloro and more preferably in the 3,4-position. It is also preferred that for the 3-position of both the $OR_3$ and $ZC(Z)R_3$ moieties, $R_3$ may also include hydrogen.

Preferably, the $R_4$ moiety is an unsubstituted or substituted phenyl moiety. More preferably, $R_4$ is phenyl or phenyl substituted at the 4-position with fluoro and/or substituted at the 3-position with fluoro, chloro, $C_{1-4}$ alkoxy, methanesulfonamido or acetamido, or $R_4$ is a phenyl di-substituted at the 3,4-position independently with chloro or fluoro, more preferably chloro. Most preferably, $R_4$ is a 4-fluorophenyl.

In Formula (I), Z is oxygen or sulfur, preferably oxygen.

Suitably, $R_2$ is $(CR_{10}R_{20})_{n'}OR_9$, heterocyclyl, heterocyclyl$C_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_{n'}SO_2R_{18}$, $(CR_{10}R_{20})_nS(O)_mNR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the cycloalkyl, cycloalkylalkyl, aryl, arylalkyl, heteroaryl, heteroarylalkyl, heterocyclic, and heterocyclic alkyl moieties may be optionally substituted; wherein n is an integer having a value of 1 to 10, m is 0, or the integer 1 or 2; n' is 0, or an integer having a value of 1 to 10; and m' is an integer having a value of 1 or 2. Preferably n is 1 to 4.

When $R_2$ is an optionally substituted heterocyclyl the ring is preferably a morpholino, pyrrolidinyl, or a piperidinyl group. When the ring is optionally substituted the substituents may be directly attached to the free nitrogen, such as in the piperidinyl group or pyrrole ring, or on the ring itself. Preferably the ring is a piperidine or pyrrole, more preferably piperidine. The heterocyclyl ring may be optionally substituted one to four times independently by halogen; $C_{1-4}$ alkyl; aryl, such as phenyl; aryl alkyl, such as benzyl— wherein the aryl or aryl alkyl moieties themselves may be optionally substituted (as in the definition section below); $C(O)OR_{11}$, such as the $C(O)C_{1-4}$ alkyl or $C(O)OH$ moieties; $C(O)H$; $C(O)C_{1-4}$ alkyl, hydroxy substituted $C_{1-4}$ alkyl, $C_{1-4}$ alkoxy, $S(O)_mC_{1-4}$ alkyl (wherein m is 0, 1, or 2), $NR_{10}R_{20}$ (wherein $R_{10}$ and $R_{20}$ are independently hydrogen or $C_{1-4}$alkyl).

Preferably if the ring is a piperidine, the ring is attached to the imidazole at the 4-position, and the substituents are directly on the available nitrogen, i.e. a 1-Formyl-4-piperidine, 1-benzyl-1-piperidine, 1-methyl-4-piperidine, 1-ethoxycarbonyl-4-piperidine. If the ring is substituted by an alkyl group and the ring is attached in the 4-position, it is preferably substituted in the 2- or 6-position or both, such as 2,2,6,6-tetramethyl-4-piperidine. Similarly, if the ring is a pyrrole, the ring is attached to the imidazole at the 3-position, and the substituents are all directly on the available nitrogen.

When $R_2$ is an optionally substituted heterocyclyl $C_{1-10}$ alkyl group, the ring is preferably a morpholino, pyrrolidinyl, or a piperidinyl group. Preferably this alkyl moiety is from 1 to 4, more preferably 3 or 4, and most preferably 3, such as in a propyl group. Preferred heterocyclic alkyl groups include but are not limited to, morpholino ethyl, morpholino propyl, pyrrolidinyl propyl, and piperidinyl propyl moieties. The heterocyclic ring herein is also optionally substituted in a similar manner to that indicated above for the direct attachment of the heterocyclyl.

When $R_2$ is an optionally substituted $C_{3-7}$cycloalkyl, or an optionally substituted $C_{3-7}$cycloalkyl $C_{1-10}$ alkyl, the cycloalkyl group is preferably a $C_4$ or $C_6$ ring, most preferably a $C_6$ ring, which ring is optionally substituted. The cycloalkyl ring may be optionally substituted one to three times independently by halogen, such as fluorine, chlorine, bromine or iodine; hydroxy; $C_{1-10}$ alkoxy, such as methoxy or ethoxy; $S(O)_m$ alkyl, wherein m is 0, 1, or 2, such as methyl thio, methylsulfinyl or methyl sulfonyl; $S(O)_m$ aryl; cyano, nitro, amino, mono & di-substituted amino, such as in the $NR_7R_{17}$ group, wherein $R_7$ and $R_{17}$ are as defined in Formula (I); $N(R_{10})C(O)R_{18}$; preferably $N(R_{10})C(O)X_1$ (wherein $R_{10}$ is as defined for Formula (I)), and $X_1$ is $C_{1-4}$ alkyl, aryl or aryl$C_{1-4}$alkyl); $C_{1-10}$ alkyl, such as methyl, ethyl, propyl, isopropyl, or t-butyl; optionally substituted alkyl wherein the substituents are halogen, (such as $CF_3$), hydroxy, nitro, cyano, amino, mono & di-$C_{1-4}$ alkyl substituted amino; $S(O)_m$ alkyl and $S(O)_m$ aryl, wherein m is 0, 1 or 2; optionally substituted alkylene, such as ethylene or propylene; optionally substituted alkyne, such as ethyne; $C(O)OR_{11}$ (wherein $R_{11}$ is as defined in Formula (I)), such as the free acid or methyl ester derivative; the group $R_c$; $C(O)H$; $=O$; $=N—OR_{11}$; $N(H)—OH$ (or substituted alkyl or aryl derivatives thereof on the nitrogen or on the oxime moiety); $N(OR_d)—C(O)—R_e$; optionally substituted aryl, such as phenyl; optionally substituted aryl$C_{1-4}$alkyl, such as benzyl of phenethyl; optionally substituted heterocycle or heterocyclic $C_{1-4}$alkyl, and further these aryl, arylalkyl, heterocyclic, and heterocyclic alkyl moieties may be optionally substituted one to two times, independently by halogen, hydroxy, $C_{1-10}$ alkoxy, $S(O)_m$ alkyl, cyano, nitro, amino, mono & di-$C_{1-4}$ alkyl substituted amino, alkyl, or halosubstituted alkyl.

Suitably the group $R_c$ is a 1,3-dioxyalkylene group of the formula —O—$(CH_2)_s$—O—, wherein s is 1 to 3, preferably s is 2 yielding a 1,3-dioxyethylene moiety, or ketal functionality.

Suitably $R_d$ is hydrogen, a pharmaceutically acceptable cation, aroyl or a $C_{1-10}$ alkanoyl group.

Suitably $R_e$ is $NR_{21}R_{22}$; $C_{1-6}$-alkyl; halosubstituted $C_{1-6}$ alkyl; hydroxy substituted $C_{1-6}$ alkyl; alkenyl 2-6; aryl or heteroaryl optionally substituted by halogen, $C_{1-6}$ alkyl, halosubstituted $C_{1-6}$ alkyl, hydroxyl, or $C_{1-6}$ alkoxy.

Suitably $R_{21}$ is H or alkyl$_{1-6}$ Suitably $R_{22}$ is H alkyl$_{1-6}$, aryl, benzyl, heteroaryl, alkyl substituted by halogen or hydroxyl, or phenyl substituted by a member selected from the group consisting of halo, cyano, alkyl$_{1-12}$, alkoxy $_{1-6}$, halosubstituted alkyl $_{1-6}$, alkylthio, alkylsulphonyl, or alkylsulfinyl; or $R_{21}$ and $R_{22}$ may together with the nitrogen to which they are attached form a ring having 5 to 7 members, which members may be optionally replaced by a heteroatom selected from oxygen, sulfur or nitrogen. The ring may be saturated or contain more than one unsaturated bond. Preferably $R_6'$ is $NR_{21}R_{22}$ and $R_{21}$ and $R_{22}$ are preferably hydrogen.

When the $R_2$ cycloalkyl moiety is substituted by $NR_7R_{17}$ group, or $NR_7R_{17}C_{1-10}$ alkyl group, and the $R_7$ and $R_{17}$ are as defined in Formula (I), the substituent is preferably an amino, amino alkyl, or an optionally substituted pyrrolidinyl moiety.

A preferred ring placement on the cyloalkyl moiety is the 4-position, such as in a $C_6$ ring. When the cycloalkyl ring is di-substituted it is preferably di-substituted at the 4 position, such as in:

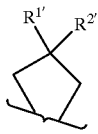

wherein $R^{1'}$ and $R^{2'}$ are independently the optional substituents indicated above for $R_2$ as an optionally substituted cycloalkyl. Preferably, $R^{1'}$ and $R^{2'}$ are hydrogen, hydroxy, alkyl, substituted alkyl, optionally substituted alkyne, aryl, arylalkyl, $NR_7R_{17}$, and $N(R_{10})C(O)R_{18}$. Suitably, alkyl is $C_{1-4}$ alkyl, such as methyl ethyl, or isopropyl; $NR_7R_{17}$ and $NR_7R_{17}$ alkyl, such as amino, methylamino, aminomethyl, aminoethyl; substituted alkyl such as in cyanomethyl, cyanoethyl, nitroethyl, pyrrolidinyl; aryl such as in phenyl; arylalkyl, such as in benzyl; optionally substituted alkyne, such as ethyne or propynyl; or together $R^{1'}$ and $R^{2'}$ are a keto functionality.

When $R_2$ is $(CR_{10}R_{20})_nNR_{13}R_{14}$, wherein $R_{13}$ and $R_{14}$ are independently selected from hydrogen, optionally substituted $C_{1-4}$ alkyl, optionally substituted aryl or an optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$. It is recognized that in some instances this can yield the same moiety as a heterocyclic $C_{1-10}$ alkyl moiety noted above which is also a suitable $R_2$ variable. Preferably $R_{13}$ and $R_{14}$ are independently hydrogen, $C_{1-4}$ alkyl, preferably methyl, or benzyl. The n term is preferably 1 to 4, more preferably 3 or 4, and most preferably 3, such as in a propyl group. Preferred groups include, but are not limited to, aminopropyl, (N-methyl-N-benzyl)aminopropyl, (N-Phenylmethyl)amino-1-propyl, or diethylamino propyl.

When $R_2$ is a $(CR_{10}R_{20})_nC(Z)OR_{11}$ group, $R_1$ is suitably hydrogen, $C_{1-4}$ alkyl, especially methyl. The n term is preferably 1 to 4, more preferably 2 or 3, such as in an ethyl or propyl group. Preferred groups include, but are not limited to, carboxymethyl-1-butyl, carboxy-1-propyl, or 2-acetoxyethyl.

When $R_2$ is a $(CR_{10}R_{20})_nS(O)_mR_{18}$ group m is 0, 1, or 2, and $R_{18}$ is preferably aryl, especially phenyl, or $C_{1-10}$ alkyl, especially methyl. The n term is preferably 1 to 4, more preferably 2 or 3, such as in an ethyl or propyl group.

When $R_2$ is a $(CR_{10}R_{20})_nOR_{11}$ group, $R_{11}$ is suitably hydrogen, aryl, especially phenyl, or $C_{1-10}$ alkyl, especially methyl or ethyl. The n term is preferably 1 to 4, more preferably 2 or 3, such as in an ethyl or propyl group.

When $R_2$ is a $(CR_{10}R_{20})_nNHS(O)_2R_{18}$ group, $R_{18}$ is suitably alkyl, especially methyl. The n term is preferably 1 to 4, more preferably 2 or 3, such as in an ethyl or propyl group.

When $R_2$ is a optionally substituted aryl, the aryl is preferably phenyl. The aryl ring may be optionally substituted one or more times, preferably by one or two substituents, independently selected from $C_{1-4}$ alkyl, halogen, especially fluoro or chloro, $(CR_{10}R_{20})_tOR_{11}$, $(CR_{10}R_{20})_tNR_{10}R_{20}$, especially amino or mono- or di-alkylamino $(CR_{10}R_{20})_tS(O)_mR_{18}$, wherein m is 0, 1 or 2; SH, $(CR_{10}R_{20})_nNR_{13}R_{14}$, $NR_{10}C(Z)R_3$ (such —NHCO($C_{1-10}$ alkyl)); $NR_{10}S(O)_mR_8$ (such as $NHSO_2(C_{1-10}$ alkyl)); and t is 0, or an integer of 1 to 4. Preferably the phenyl is substituted in the 3 or 4-position by $(CR_{10}R_{20})_tS(O)_mR_{18}$, and $R_{18}$ is preferably $C_{1-10}$ alkyl, especially methyl.

When $R_2$ is an optionally substituted heteroaryl or heteroarylalkyl group the ring may be optionally substituted one or more times, preferably by one or two substituents, independently selected from one or more times, by $C_{1-4}$ alkyl, halogen, especially fluoro or chloro, $(CR_{10}R_{20})_tOR_{11}$, $(CR_{10}R_{20})_tNR_{10}R_{20}$, especially amino or mono- or di-alkylamino —$CR_{10}R_{20})_tS(O)_mR_{18}$, wherein m is 0, 1 or 2; SH, $(CR_{10}R_{20})_n$—$NR_{13}R_{14}$, $NR_{10}C(Z)R_3$ (such NHCO ($C_{1-10}$ alkyl)); $NR_{10}S(O)_mR_8$ (such as —$NHSO_2(C_{1-10}$ alkyl)); t is 0, or an integer of 1 to 4.

One skilled in the art would readily recognize that when $R_2$ is a $(CR_{10}R_{20})_nOC(Z)R_{11}$, or $(CR_{10}R_{20})_nOC(Z)NR_{13}R_{14}$ moiety, or any similarly substituted group that n is preferably at least 2 which will allow for the synthesis of stable compounds.

Preferably $R_2$ is an optionally substituted heterocyclyl ring, and optionally substituted heterocyclyl$C_{1-10}$ alkyl, an optionally substituted $C_{1-10}$ alkyl, an optionally substituted $C_{3-7}$cycloalkyl, an optionally substituted $C_{3-7}$cycloalkyl $C_{1-10}$ alkyl, $(CR_{10}R_{20})_nC(Z)OR_{11}$ group, $(CR_{10}R_{20})_nNR_{13}R_{14}$, $(CR_{10}R_{20})_nNHS(O)_2R_{18}$, $(CR_{10}R_{20})_nS(O)_mR_{18}$, an optionally substituted aryl; an optionally substituted aryl$C_{1-10}$ alkyl, $(CR_{10}R_{20})_nOR_{11}$, $(CR_{10}R_{20})_nC(Z)R_{11}$, or $(CR_{10}R_{20})_nC(=NOR_6)R_{11}$ group.

More preferably $R_2$ is an optionally substituted heterocyclyl ring, and optionally substituted heterocyclyl$C_{1-10}$ alkyl, optionally substituted aryl, optionally substituted $C_{3-7}$cycloalkyl, optionally substituted $C_{3-7}$cycloalkyl $C_{1-10}$ alkyl, $(CR_{10}R_{20})_nNR_{13}R_{14}$, or $(CR_{10}R_{20})_nC(Z)OR_{11}$ group. Most preferably $R_2$ is an optionally substituted heterocyclic, heterocyclic $C_{1-4}$ alkyl, a cycloalkyl or a cycloalkyl alkyl.

More preferably when $R_2$ is an optionally substituted cycloalkyl or cycloalkylalkyl it is a $C_4$ or $C_6$ cycloalkyl, cyclopropyl methyl, or a cyclohexyl substituted by methyl, phenyl, benzyl, amino, acetamide, aminomethyl, aminoethyl, cyanomethyl, cyanoethyl, hydroxy, nitroethyl, pyrrolidinyl, ethynyl, 1-propynyl, =O, O—(CH$_2$)$_2$O—, =NOR$_{11}$, wherein R$_{11}$ is hydrogen, alkyl or aryl, NHOH, or N(OH)—C(O)—NH$_2$; or when R$_2$ is heterocyclic, or heterocyclicalkyl, it is morpholinyl butyl, morpholinyl propyl, morpholinylethyl, piperidinyl, N-benzyl-4-piperidinyl, N-methyl-4-piperidinyl, 2,2,6,6-tetramethypiperidinyl, substituted piperidine, such as 1-Formyl-4-piperidine, or a 1-ethoxycarbonyl-4-piperidine.

In all instances herein where there is an alkenyl or alkynyl moiety as a substituent group, the unsaturated linkage, i.e., the vinylene or acetylene linkage is preferably not directly attached to the nitrogen, oxygen or sulfur moieties, for instance in OR$_3$, or for certain R$_2$ moieties.

As used herein, "optionally substituted" unless specifically defined shall mean such groups as halogen, such as fluorine, chlorine, bromine or iodine; hydroxy; hydroxy substituted C$_{1-10}$alkyl; C$_{1-10}$ alkoxy, such as methoxy or ethoxy; S(O)m alkyl, wherein m is 0, 1 or 2, such as methyl thio, methylsulfinyl or methyl sulfonyl; amino, mono & di-C$_{1-4}$ alkyl substituted amino, such as in the NR$_7$R$_{17}$ group; or where the R$_7$R$_{17}$ may together with the nitrogen to which they are attached cyclize to form a 5 to 7 membered ring which optionally includes an additional heteroatom selected from O/N/S; C$_{1-10}$ alkyl, cycloalkyl, or cycloalkyl alkyl group, such as methyl, ethyl, propyl, isopropyl, t-butyl, etc. or cyclopropyl methyl; halosubstituted C$_{1-10}$ alkyl, such CF$_3$; halosubstituted C$_{1-10}$ alkoxy, such OCF$_2$CF$_2$H, or OCF$_3$; an optionally substituted aryl, such as phenyl, or an optionally substituted arylalkyl, such as benzyl or phenethyl, wherein these aryl moieties may also be substituted one to two times by halogen; hydroxy; hydroxy substituted alkyl; C$_{1-10}$ alkoxy; S(O)$_m$ alkyl; amino, mono & di-substituted amino, such as in the NR$_7$R$_{17}$ group; alkyl, or CF$_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:

"halo" or "halogens", include the halogens: chloro, fluoro, bromo and iodo.

"C$_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

"cycloalkyl" is used herein to mean cyclic radicals, preferably of 3 to 8 carbons, including but not limited to cyclopropyl, cyclopentyl, cyclohexyl, and the like.

"cycloalkenyl" is used herein to mean cyclic radicals, preferably of 5 to 8 carbons, which have at least one bond including but not limited to cyclopentenyl, cyclohexenyl, and the like.

"alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclylalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

"aralkyl" or "heteroarylalkyl" or "heterocyclicalkyl" is used herein to mean C$_{1-4}$ alkyl as defined above attached to an aryl, heteroaryl or heterocyclic moiety as also defined herein unless otherwise indicate.

"sulfinyl"—the oxide S(O) of the corresponding sulfide, the term "thio" refers to the sulfide, and the term "sulfonyl" refers to the fully oxidized S(O)$_2$ moiety.

"aroyl"—a C(O)Ar, wherein Ar is as phenyl, naphthyl, or aryl alkyl derivative such as defined above, such group include but are not limited to benzyl and phenethyl.

"alkanoyl"—a C(O)C$_{1-10}$ alkyl wherein the alkyl is as defined above.

It is recognized that the compounds of the present invention may exist as stereoisomers, regioisomers, or diastereisomers. These compounds may contain one or more asymmetric carbon atoms and may exist in racemic and optically active forms. All of these compounds are included within the scope of the present invention.

Another aspect of the present invention are the novel compounds exemplified below:

1-Cyclohexyl-4-(4-fluorophenyl)-5-[(2-phenylamino) pyrimidin-4-yl]imidazole;

1-Cyclohexyl-4-(4fluorophenyl)-5-[[2[N-(3-morpholino) propyl]amino]pyrimidin-4-yl]imidazole;

1-Cyclohexyl-4-(4-fluorophenyl)-5-[[2-[N-(2-imidazol-4-yl)ethyl]amino]pyrimidin-4-yl]imidazole;

1-Cyclohexyl-4-(4-fluorophenyl)-5-[[2-[N-(3-pyridyl) methyl]amino]pyrimidin-4-yl]imidazole;

1-Cyclohexyl-4(4-fluorophenyl)-5-[[2-[N-(3,3-diphenyl) propyl]amino]pyrimidin-4-yl]imidazole;

(±)-1-Cyclohexyl-4-(4-fluorophenyl)-5-[[2-[N-(1-methyl-3-phenyl)propyl]amino]pyrimidin-4-yl]imidazole;

N-4-[[[4-(4-Fluorophenyl)]-5-[[2-[(3-trifluoromethyl) phenyl]amino]]pyrimidine-4-yl]imidazol-4-yl] piperdinyl-N'-[(3-trifluoromethyl)phenyl]urea;

N-[2-[4-(4-Fluorophenyl)-5-[[2-(3,4-dichlorobenzyl) pyrimidin-4-yl]-1H-imidazol-1-yl]ethyl]-3,4-dimethoxybenzamide;

N-[2-[4-(4-Fluorophenyl)-5-[[2-(4-methoxybenzylamino) pyrimidin-4-yl]-1H-imidazol-1-yl]ethyl]-ethoxyacetamide;

1-Isopropyl-4-(4-fluorophenyl)-5-[2-phenylamino-pyrimidin-4-yl]imidazole;
1-Cyclopentyl-4-(4-fluorophenyl)-5-[2-phenylamino-pyrimidin-4-yl]imidazole;
1-[(1-t-Butoxycarbonyl)-4-piperidinyl]-4-(4-fluorophenyl)-5-[2-(2-methyl-4-fluorophenyl)amino]pyrimidin-4-yl]imidazole;
1-(4-Piperidinyl)-4-(4-fluorophenyl)-5-[2-(2-methyl-4-fluorophenyl)-amino]pyrimidin-4-yl]imidazole;
1-(4-Piperidinyl)-4-(4-fluorophenyl)-5-[2-(2-methyl-5-fluorophenyl)amino]pyrimidin-4-yl]imidazole;
1-(4-Piperidinyl)-4-(4-fluorophenyl)-5-[2-(2,6-dimethylphenyl)amino]pyrimidin-4-yl]imidazole;
1-(4-Piperidinyl)-4-(4-fluorophenyl)-5-[2-(2-methylphenyl)amino]pyrimidin-4-yl]imidazole;
1-(4-Fluorophenyl)-4-(4-fluorophenyl)-5-[2-phenylamino-pyrimidin-4-yl]imidazole;
1-(4-Fluorophenyl)-4-(4-fluorophenyl)-5-[2-(4-fluorophenylamino)-pyrimidin-4-yl]imidazole;
1-(4-Fluorophenyl)-4-(4-fluorophenyl)-5-[2-(4-methylphenylamino)-pyrimidin-4-yl]imidazole;
1-(4-Fluorophenyl)-4-(4-fluorophenyl)-5-[2-(2-methylphenylamino)pyrmidin-4-yl]imidazole;
1-(4-Fluorophenyl)-4-(4-fluorophenyl)-5-[2-(2,6-dimethylphenylamino)pyrimidin-4-yl]imidazol;
1-(4-Fluorophenyl)-4-(4-fluorophenyl)-5-[2-(4-morpholin-4-ylphenylamino)pyrimidin-4-yl]imidazole; or
a pharmaceutically acceptable salt thereof Another aspect of the present invention is the novel pharmaceutical compositions comprising a pharmacuetically acceptable diluent or carrier, and an effective amount of an exemplified compound defined above.

Another aspect of the present invention relates to a method of treating a CSBP/RK/p38 kinase mediated disease, in a mammal in need thereof which comprises administering to said mammal an effective amount of an exemplified compound as described above.

This invention also relates to a method of inhibiting cytokines and the treatment of a cytokine mediated disease, in a mammal in need thereof which comprises administering to said mammal an effective amount of an exemplified compound as described above.

This invention more specifically relates to a method of inhibiting the production of IL-1 in a mammal in need thereof which comprises administering to said mammal an effective amount of an exemplified compound as described above.

This invention more specifically relates to a method of inhibiting the production of IL-8 in a mammal in need thereof which comprises administering to said mammal an effective amount of an exemplified compound as described above.

This invention more specifically relates to a method of inhibiting the production of TNF in a mammal in need thereof which comprises administering to said mammal an effective amount of an exemplified compound as described above.

Another aspect of the present invention relates to a process for producing the exemplified compounds noted above. For simplicity the exemplified compounds are summarized in the table below.

The present invention relates to an analagous process for making compounds of the formula:

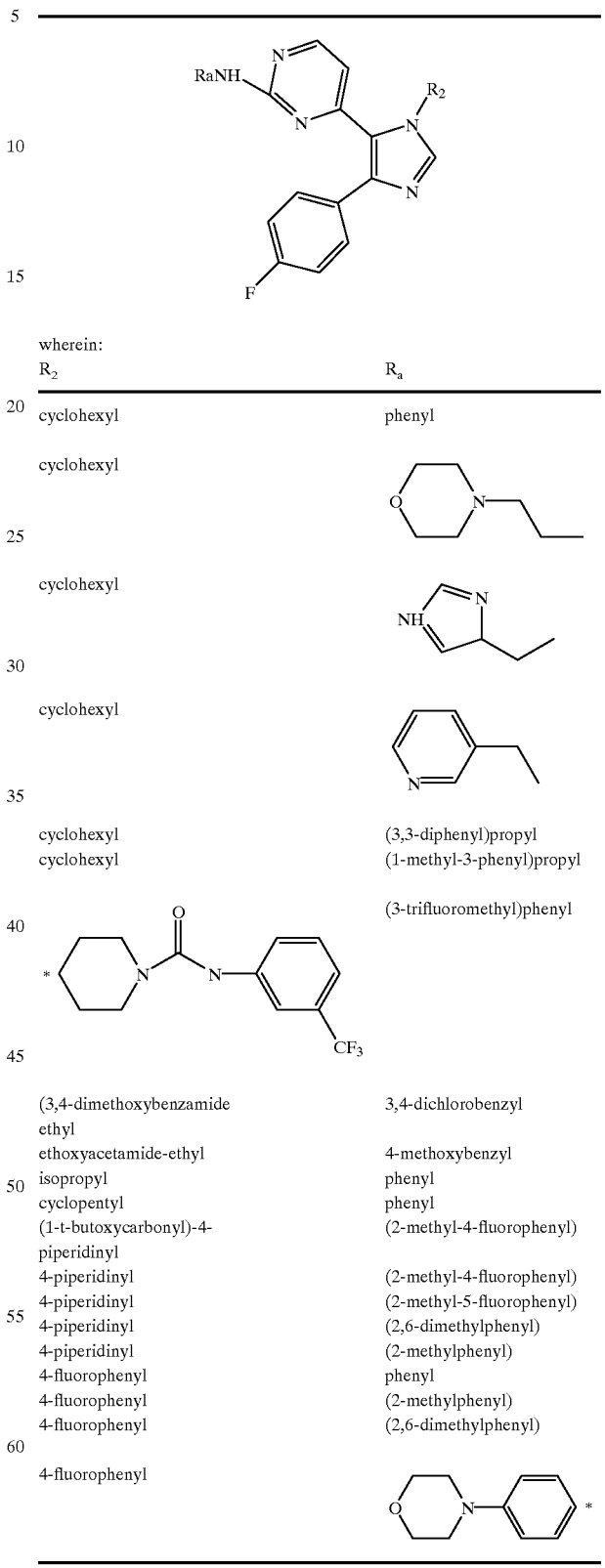

wherein:

| $R_2$ | $R_a$ |
|---|---|
| cyclohexyl | phenyl |
| cyclohexyl | (morpholinyl-propyl group) |
| cyclohexyl | (imidazolyl-ethyl group) |
| cyclohexyl | (pyridinyl-ethyl group) |
| cyclohexyl | (3,3-diphenyl)propyl |
| cyclohexyl | (1-methyl-3-phenyl)propyl |
|  | (3-trifluoromethyl)phenyl |
|  | (piperidinyl carboxamide-CF3-phenyl group) |
| (3,4-dimethoxybenzamide ethyl | 3,4-dichlorobenzyl |
| ethoxyacetamide-ethyl | 4-methoxybenzyl |
| isopropyl | phenyl |
| cyclopentyl | phenyl |
| (1-t-butoxycarbonyl)-4-piperidinyl | (2-methyl-4-fluorophenyl) |
| 4-piperidinyl | (2-methyl-4-fluorophenyl) |
| 4-piperidinyl | (2-methyl-5-fluorophenyl) |
| 4-piperidinyl | (2,6-dimethylphenyl) |
| 4-piperidinyl | (2-methylphenyl) |
| 4-fluorophenyl | phenyl |
| 4-fluorophenyl | (2-methylphenyl) |
| 4-fluorophenyl | (2,6-dimethylphenyl) |
| 4-fluorophenyl | (morpholinyl-phenyl group) |

*denoting point of attachment which process comprises reacting a compound of the formula:

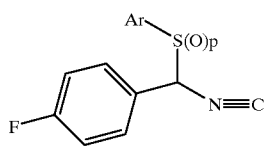
(IIa)

with a compound of the formula:

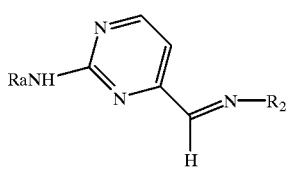
(III)

wherein p is 2; Ar is an unsubstituted or substituted aryl; and $R_a$ and $R_2$ are as described above; with a base strong enough to deprotonate the isonitrile moiety of Formula (IIa); and wherein the imine of Formula (III), is formed in situ prior to reaction with Formula (IIa); to yield a compound as defined in the table above. Suitably, the Ar is a phenyl optionally substituted by $C_{1-4}$alkyl, $C_{1-4}$ alkoxy or halogen. Preferably, Ar is phenyl or 4-methylphenyl, i.e. a tosyl derivative.

In this process the base is preferably an amine, an amide, a carbonate, a hydride, an alkyl or aryl lithium reagent, or a mono-, di- or tribasic phosphate.

The imine of this reaction is preferably formed in situ by reacting an aldehyde of the formula:

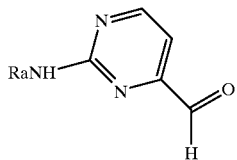

wherein $R_a$ is as defined above, with a primary amine of the formula $R_2NH_2$, wherein $R_2$ is as defined above.

In this process the formation of the imine in situ may utilize dehydrating conditions as can be found in the numerous patents referenced herein. Preferably, solvents used in this process are N,N-dimethyl-formamide (DMF), halogenated solvents, tetrahydrofuran (THF), dimethylsulfoxide (DMSO), an alcohol, benzene, toluene, MeCN, or DME.

The intermediates of Formula (II) may suitably be made as described in U.S. Pat. No. 5,739,143, see Scheme VIII; and WO 97/23479.

In an alternative synthesis to make the novel exemplified compounds of the formula:

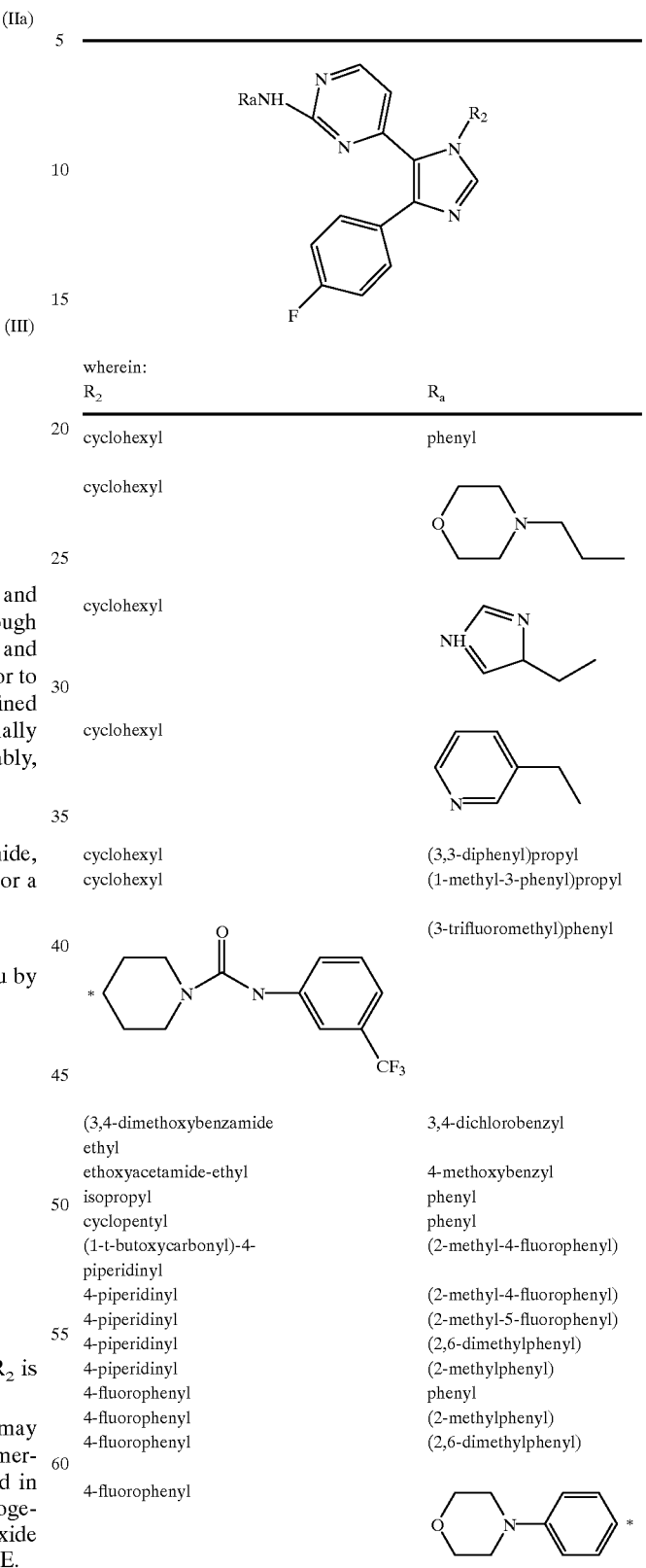

*denoting point of attachment;

which process comprises reacting a compound of the formula:

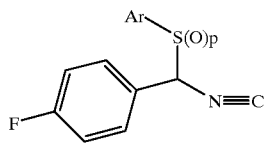
(IIa)

with a compound of the formula:

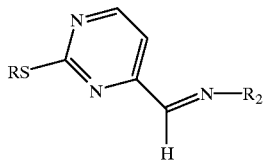
(IIIa)

wherein R is a substituted or unsubstituted $C_{1-4}$ alkyl, Ar is an unsubstituted or substituted aryl; $R_2$ is as defined above, and p is =2; to yield a compound of the formula:

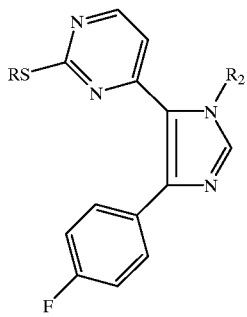

wherein R and $R_2$ are as defined above;
and using suitable oxidizing conditions to make the corresponding sulfone or sulfoxide derivative; and using suitable displacement conditions reacting the corresponding sulfone or sulfoxide derivative with the desired activated $NH_2R_a$ moiety, or a precurser thereof such as the metal salt, i.e. the activated lithium or aluminum complex, to yield a compound as defined in the table above. Suitably, the Ar is a phenyl optionally substituted by $C_{1-4}$ alkyl, $C_{1-4}$ alkoxy or halogen. Preferably, Ar is phenyl or 4-methylphenyl, i.e. a tosyl derivative.

Suitable oxidizing conditions are well known in the art, and may be found in, for instance U.S. Pat. No. 5,756,499. While it is recognized that in Scheme VI therein the oxidation and displacement of the RS moiety on the pyrimidine takes place prior to the imidazole formation, but the same general conditions would apply herein. Oxone is a preferred oxidation reagent to convert the alkylthio deriviative to the corresponding sulfone, or sulfoxide, or both (Formula IIIa).

Displacement of the oxidized sulfone or sulfoxide derivative is also well known in the art. Suitably, activation of the desired aniline ($Ra$—$NH_2$) with trimethyl aluminum yields the aluminum amide complex. Reaction of this complex with the oxidizied sulfoxide or sulfone of Formula (IIIa) will generate the desired compounds herein of Formula (III). Alternatively, the aniline may be reacted with a strong base, such as butyl lithium or LDA directly, and then reacted with the sulfoxide or sulfone will generate the desired compounds herein.

The novel compounds of Formula (I) and the specifically exemplified compounds herein may also be obtained by applying various synthetic procedures, some of which are described in U.S. Pat. No. 5,658,903, U.S. Ser. No. 09/012,946 (now allowed), U.S. Pat. Nos. 5,739,143, 5,716,955, and 5,593,992 whose disclosures are incorporated herein by reference in their entirety.

An alternative process for preparing the above exemplified compounds, and compounds of Formula (A), as described herein, is by using solid-phase techniques as shown below.

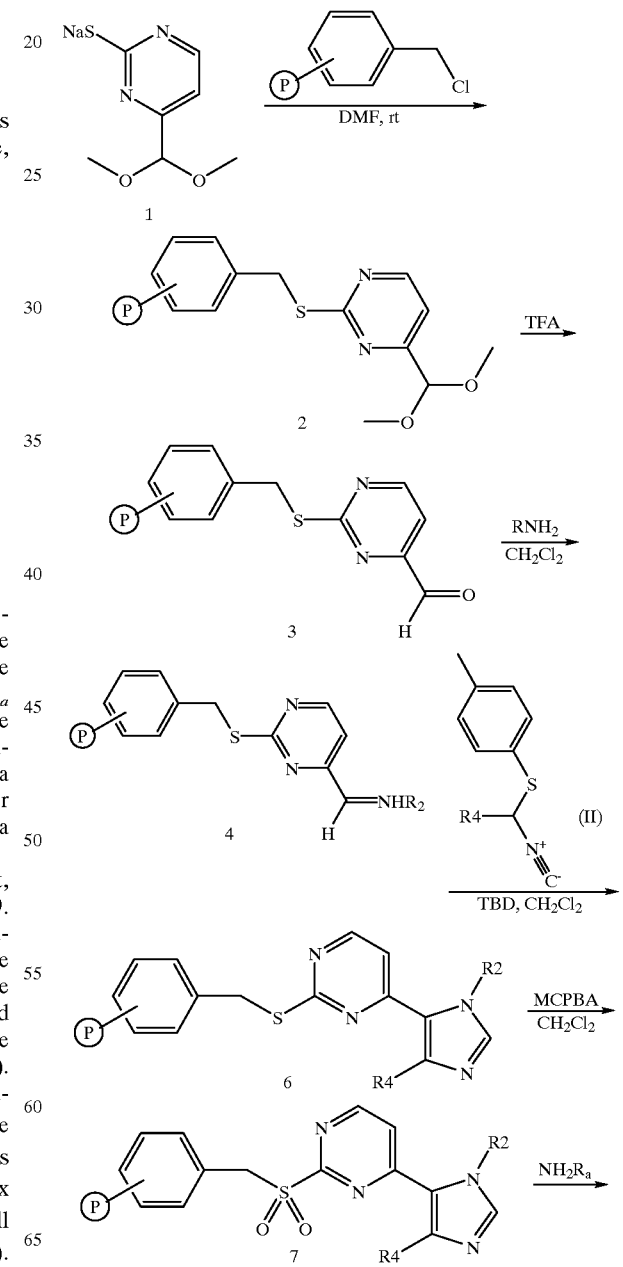

-continued

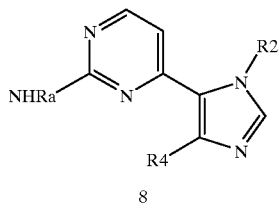

8

In this scheme sodium 2-thiopyrimidine-4-dimethyl acetal (1) can be treated with Merrifield resin in DMF at room temperature to afford polymer-bound pyrimidine acetal (2) in nearly quantitative yield. Treatment of 2 with TFA either at room temperature or by heating to reflux efficiently affords polymer-bound aldehyde 3. Condensation of 3 with $NH_2R_2$, wherein $R_2$ is as defined in formula (I) or (A) affords the corresponding polymer-bound imines 4. Cycloaddition of 4 with isonitriles of formula (II) in the presence of a strong base such as TDB, which is soluble in an organic solvent which will swell the resin such as DMF, affords polymer-bound 2-thiopyrimidinyl-imidazoles 6. The desired compound of Formula (A)(8) can be released from the polymer by first oxidizing 6 to the corresponding sulfone (7) using, for instance, 3-chloroperoxybenzoic acid followed by treatment with $NH_2R_a$. In cases in which the amine is aliphatic, the displacement simply requires stirring the sulfone 7 with the amine at temperatures ranging from ambient to 100° C. Displacement with anilines requires activation with a strong base such as sodium hydride or a lewis acid such as trimethylaluminum followed by heating in an inert solvent such as THF or toluene.

Another aspect of the present invention, therefore, is the novel process for preparing 2-thiopyrmidin-4-yl imidazoles derivatives on a solid support, such as a Merrifield resin. This process involves the cycloaddition of a polymer-bound 2-thiopyrimidin-4-yl carboxaldehyde (imines) with suitable isonitriles (II) as depicted in Scheme I and the characteristics of which have been described previously, in U.S. Pat. No. 5,658,903, to give polymer-bound 2-thiopyrimidine-4yl imidazoles. This is followed by cycloaddition of the polymer-bound imines with a suitable isonitrile (II) which can be conducted at temperatures from −10 to 100° C., but requires a solvent, such as $CH_2Cl_2$, which will swell the resin, and a base which is soluble in this solvent, such as TBD. The reaction may also be conducted using other solvents which swell the resin such as DMF, dioxane or TBF. Other organic soluble bases such as the heterocyclic bases DBU and DBN as well as primarily amines such as t-butylamine may be substituted for TBD. Use of conditions such as $K_2CO_3$ in DMF, which work well in solution, fail to effect cycloaddition with the polymer-bound imines. Liberation of the polymer-bound 2-thiopynmidine-4yl imidazoles to give 2-aminopyrimidin-4-yl imidazole derivatives of Formula (I) or (A) can be accomplished by the following two step process: 1) Polymer-bound 2-thiopyrimidine-4-yl imidazoles can be oxidized to either the corresponding sulfoxides or sulfones (or a mixture of the two) by treatment of the polymer-bound sulfide with an organic soluble oxidant such as 3-chloro-peroxybenzoic acid or and organic soluble oxone, such as tetrabutylammonium oxone, in a solvent which will swell the resin, such as $CH_2Cl_2$; and 2) Treatment of either the sulfoxides or sulfones with amines of the formula $R_aNH_2$, wherein $R_a$ is defined in Formula (I) or (A) at temperatures ranging from about 0 to 120° C., or even higher to 150° C. affords compounds of Formula (A).

Preparation of polymer-bound 2-thiopyrimidin-4-yl carboxaldehyde(imines) require, first of all, preparation of polymer-bound 2-thiopyrimidine-4-yl carboxaldehyde dimethyl acetal. The sodium salt of 2-thiopyrimidine-4-yl carboxaldehyde dimethyl acetal can be prepared as outlined in the Scheme, herein. Stirring or shaking the salt with Merrifield resin at temperatures ranging from 10 to 100° C. in a solvent which both swells the resin and dissolves the salt, for instance DMF, affords a nearly quantitative loading of the pyrimidine on the resin. The dimethylacetal can be hydrolyzed to the aldehyde with out effecting the thio linker by reaction at temperatures ranging from 20 to 80° C. with a strong acid, such as TFA, which can also serve to swell the resin. Conversion of the polymer-bound aldehyde to the desired imines can be achieved by simply stirring the desired amine ($R_2NH_2$) as indicated in Formula (I) or (A) with polymer-bound aldehyde in an inert resin-swelling solvent such as $CH_2Cl_2$ at temperatures ranging from 0 to 60° C.

Pharmaceutically acid addition salts of compounds of Formula (I) or (A) may be obtained in known manner, for example by treatment thereof with an appropriate amount of acid in the presence of a suitable solvent.

Compounds of Formula (A) are described as compounds of Formula (I) in U.S. Pat. No. 5,658,903, and are the same as those described for Formula (I) herein but for the substitution of a 4-pyrimidinyl ring for the $R_1$ pyridazin-4-yl or 1,2,4-triazin-5-yl substituents defined herein. It is also recognized that the exemplified compounds above, all fall within the genus of compounds described as Formula (A).

Compounds of Formula (A) are represented by the structure:

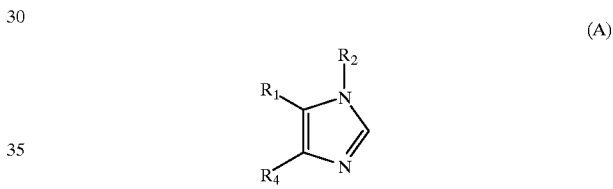

(A)

wherein
$R_1$ is 4-pyrimidinyl ring which ring is substituted with $NHR_a$ and optionally substituted with an additional, independent, substituent of $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, $N(R_{10})C(O)R_b$ or $NHR_a$;

$R_a$ is hydrogen, alkyl, optionally substituted alky, aryl, aryl$C_{1-6}$alkyl, heterocyclic, heterocyclyl$C_{1-6}$ alkyl, heteroaryl, or heteroaryl$C_{1-6}$alkyl, wherein each of the aryl, heterocyclic and heteroaryl containing moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_6$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_3$, halo-substituted-$C_{1-4}$ alkyl, $C_{1-4}$ alkyl, $(CR_{10}R_{20})_{m''}NR_{10}C(Z)R_3$, $NR_{10}S(O)_{m'}R_8$, $NR_{10}S(O)_{m'}NR_7R_{17}$, $ZC(Z)R_3$ or $(CR_{10}R_{20})_{m''}NR_{13}R_{14}$;

v is 0, or an integer having a value of 1 or 2;

m is 0, or the integer 1 or 2;

m' is an integer having a value of 1 or 2, m" is 0, or an integer having a value of 1 to 5;

$R_2$ is —$(CR_{10}R_{20})_{n'}$ $OR_9$, heterocyclyl, heterocyclyl$C_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$cycloalkenyl-$C_{1-10}$-alkyl, aryl, aryl$C_{1-10}$ alkyl, heteroaryl, heteroaryl-$C_{1-10}$-alkyl $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_{n'}SO_2R_{18}$, $(CR_{10}R_{20})_nS(O)_{m'}NR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-$(R_{18})$-1,2,4-oxadizaol-3-yl or 4-$(R_{12})$-5-$(R_{18}R_{19})$-4,5-dihydro-1,2,4-oxadiazol-3-yl; wherein the aryl, arylalkyl, heteroaryl, heteroaryl alkyl, cycloalkyl, cycloalkyl alkyl, heterocyclic and heterocyclic alkyl groups may be optionally substituted;

n is an integer having a value of 1 to 10;

n' is 0, or an integer having a value of 1 to 10;

Z is oxygen or sulfur;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$_{1-4}$alkyl, heterocyclyl, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; wherein the aryl, arylalkyl, heteroaryl, heteroaryl alkyl may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is $R_{10}$ or $C(Z)$-$C_{1-4}$ alkyl;

$R_{16}$ is $C_{1-4}$ alkyl, halo-substituted-$C_{1-4}$alkyl or $C_{3-7}$ cycloalkyl;

$R_{18}$ is $C_{1-10}$ alkyl, $C_{3-7}$ cycloalkyl, heterocyclyl, aryl, aryl$_{1-10}$alkyl, heterocyclyl, heterocyclyl-$C_{1-10}$ alkyl, heteroaryl or heteroaryl$_{1-10}$alkyl;

$R_{19}$ is hydrogen, cyano, $C_{1-4}$ alkyl, $C_{3-7}$ cycloalkyl or aryl;

or a pharmaceutically acceptable salt thereof.

METHODS OF TREATMENT

The compounds of Formula (I), or the above noted exemplified compounds herein, or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

For purposes herein in the Method of Treatment section, compounds of Formula (I) and the novel exemplified compounds are used interchangeably. The methods of formulation, dosage forms, disease management, etc. are the same for both formulas. For instance, "Compounds of Formula (I) are capable . . . " is also the same as stating: "Compounds of Formula (I) and the novel compounds as exemplified herein, are capable . . . ".

Compounds of Formula (I) are capable of inhibiting proinflammatory cytokines, such as IL-1, IL-6, IL-8 and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of Formula (I) or a pharmaceutically acceptable salt thereof Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof The present invention also provides for a method of prophylaxis treatment in a human, or other mammal, by inhibition of the synthesis of the COX-2 enzyme.

A new member of the MAP kinase family, alternatively termed CSBP, p38, or RK, has been identified independently by several laboratories recently. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I), have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages.

The cytokine inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 23 31:1406–1412; Badger, et al., (1989) *Circ. Shock* 27, 51–61; Votta et al., (1994) in vitro. *Bone* 15, 533–538; Lee et al., (1993). *B Ann. N. Y. Acad Sci.* 696, 149–170.

Another aspect of the present invention, therefore, is the treatment of a CSBP/RK/p38 kinase mediated disease, in a mammal in need thereof, which comprises administering to said mammal an effective amount of a compound of Formula (I). Suitable diseases, include those mentioned herein for IL-1, IL-6, IL-8 and TNF and more specifically those disease which are CSBP/RK/p38 kinase mediated diseases. These include, but are not limited to rheumatoid arthritis, rheumatoid spondylitis, osteoarthritis, gouty arthritis and other arthritic conditions, sepsis, septic shock, endotoxic shock, gram negative sepsis, toxic shock syndrome, asthma, adult respiratory distress syndrome, stroke, reperfusion injury, CNS injuries, such as neurotrauma and ischemia, including both open and closed head injuries), psoriasis, restenosis, such as occurs following coronary angioplasty, cerebral malaria, chronic pulmonary inflammatory disease, silicosis, pulmonary sarcososis, bone resorption diseases, osteoporosis, , graft vs. host reaction, allograft rejections, Crohn's disease, ulcerative colitis or any other anti-inflammatory bowel disease (IBD), or pyresis.

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this are has been emerging and the present invention provides a mean for the potential treatment of these injuries. Relatively little treatment, for an acute injury such as these has been available.

TNF-α is a cytokine with proinflammatory actions, including endothelial leukocyte adhesion molecule expression. Leukocytes infiltrate into ischeric brain lesions and hence compounds which inhibit or decrease levels of TNF would be useful for treatment of ischernic brain injury. See Liu et al., Stoke, Vol. 25., No. 7, pp. 1481–88 (1994) whose disclosure is incorporated herein by reference.

Models of closed head injuries and treatment with mixed 5-LO/CO agents is discussed in Shohami et al., J. of Vaisc & Clinical Physiology and Pharmacology, Vol. 3, No. 2, pp. 99–107 (1992) whose disclosure is incorporated herein by reference. Treatment which reduced edema formation was found to improve functional outcome in those animals treated.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arhritis, Reiter's syndrome, rheumatoid arthritis, gout, traumatic arthritis, rubella arthritis and acute synovitis. Recent evidence also links IL-1 activity to diabetes, pancreatic β cells and Alzheimer's disease.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, stroke, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (1L-6, 1L-8 or TNF)" refers to:

a) a decrease of excessive in vivo levels of the cytokine (IL-1, IL-6, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lympholines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNFα) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytoldne referred to in the phrase "inhibition of a cytokine, for use in the treatment of a HIV-infected human" is a cytokine which is implicated in (a)

the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-a and TNF-β are inhibited by the compounds of the present invention and thus are herein referred to collectively as "TNF" unless specifically delineated otherwise.

In order to use a compound of Formula (I) or a pharmaceutically acceptable salt thereof in therapy, it will normally be Formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the Formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0.1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.01 to about 80 mg/kg of total body weight, preferably from about 0.1 to 30 mg/kg, more preferably from about 0.2 mg to 15 mg. The daily parenteral dosage regimen about 0.01 to about 80 mg/kg of total body weight, preferably from about 0.1 to about 30 mg/kg, and more preferably from about 0.2 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The novel compounds of Formula (I) may also be used in association with the veterinary treatment of mammals, other than humans, in need of inhibition of cytokine inhibition or production. In particular, cytokine mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The invention will now be described by reference to the following biological examples which are merely illustrative and are not to be construed as a limitation of the scope of the present invention.

BIOLOGICAL EXAMPLES

The cytokine-inhibiting effects of compounds of the present invention were determined by the following in vitro assays:

Interleukin-1 (IL-1)

Human peripheral blood monocytes are isolated and purified from either fresh blood preparations from volunteer donors, or from blood bank buff coats, according to the procedure of Colotta et al, J Immunol, 132, 936 (1984). These monocytes (1×10⁶) are plated in 24-well plates at a concentration of 1–2 million/ml per well. The cells are allowed to adhere for 2 hours, after which time non-adherent cells are removed by gentle washing. Test compounds are then added to the cells for 1 h before the addition of lipopolysaccharide (50 ng/ml), and the cultures are incubated at 37° C. for an additional 24 h. At the end of this period, culture supernatants are removed and clarified of cells and all debris. Culture supernatants are then immediately assayed for IL-1 biological activity, either by the method of Simon et al., J. Immunol. Methods, 84, 85, (1985) (based on ability of IL-1 to stimulate a Interleukin 2 producing cell line (EL-4) to secrete IL-2, in concert with A23187 ionophore) or the method of Lee et al., J. Immuno Therapy, 6 (1), 1–12 (1990) (ELISA assay).

Tumour Necrosis Factor (TNF)

Human peripheral blood monocytes are isolated and purified from either blood bank buffy coats or plateletpheresis residues, according to the procedure of Colotta, R. et al., J Immunol, 132(2), 936 (1984). The monocytes are plated at a density of 1×10⁶ cells/ml medium/well in 24-well multidishes. The cells are allowed to adhere for 1 hour after which time the supernatant is aspirated and fresh medium (1 ml, RPMI-1640, Whitaker Biomedical Products, Whitaker, Calif.) containing 1% fetal calf serum plus penicillin and streptomycin (10 units/ml) added. The cells are incubated for 45 minutes in the presence or absence of a test compound at 1 nM–10 mM dose ranges (compounds are solubilized in dimethyl sulfoxide/ethanol, such that the final solvent concentration in the culture medium is 0.5% dimethyl sulfoxide/ 0.5% ethanol). Bacterial lipopoly-saccharide (*E. coli* 055:B5 [LPS] from Sigma Chemicals Co.) is then added (100 ng/ml in 10 ml phosphate buffered saline) and cultures incubated for 16–18 hours at 37° C. in a 5% $CO_2$ incubator. At the end of the incubation period, culture supernatants are removed from the cells, centrifuged at 3000 rpm to remove cell debris. The supernatant is then assayed for TNF activity using either a radio-immuno or an ELISA assay, as described in WO 92/10190 and by Becker et al., J Immunol, 1991, 147, 4307.

IL-1 and TNF inhibitory activity does not seem to correlate with the property of the compounds of Formula (I) in mediating arachidonic acid metabolism inhibition. Further the ability to inhibit production of prostaglandin and/or leukotriene synthesis, by nonsteroidal anti-inflammatory drugs with potent cyclooxygenase and/or lipoxygenase inhibitory activity does not mean that the compound will necessarily also inhibit TNF or IL-1 production, at non-toxic doses.

In vivo TNF Assay

While the above indicated assay in an in vitro assay, the compounds of Formula (I) may also be tested in an in vivo system such as described in:

(1) "Differentiation In Vivo of Classical Non-Steroidal Antiinflammatory Drugs from Cytokine Suppressive Antiinflammatory Drugs and Other Pharmacological Classes Using Mouse Tumour Necrosis Factor Alpha Production", Griswold et al., *Drugs Under Exp. and Clinical Res., XIX* (6), 243–248 (1993); or in (2) Boehm, ea al., 1-substituted 4aryl-5-pyridinylimidazoles—a new class of cytokine suppressive drugs with low 5-lipoxygenase and cyclooxygenase inhibitory potency. *Journal Of Medicinal Chemistry* 39, 3929–3937 (1996) whose disclosures are incorporated by reference herein in their entirety.

Interleukin-8 (IL-8)

Primary human umbilical cord endothelial cells (HUVEC) (Cell Systems, Kirland, Wash.) are maintained in culture medium supplemented with 15% fetal bovine serum and 1% CS-HBGF consisting of AFGF and heparin. The cells are then diluted 20-fold before being plated (2501 µl) into gelating coated 96-well plates. Prior to use, culture medium are replaced with fresh medium (200 µl). Buffer or test compound (25 µl, at concentrations between 1 and 10 µM) is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/ml) of multiple samples based on the standard curve. $IC_{50}$'s where appropriate are generated by non-linear regression analysis.

Cytokine Specific Binding Protein Assay

A radiocompetitive binding assay was developed to provide a highly reproducible primary screen for structure-activity studies. This assay provides many advantages over the conventional bioassays which utilize freshly isolated human monocytes as a source of cytokines and ELISA assays to quantify them. Besides being a much more facile assay, the binding assay has been extensively validated to highly correlate with the results of the bioassay. A specific and reproducible cytokine inhibitor binding assay was developed using soluble cystosolic fraction from THP.1 cells and a radiolabeled compound. patent application Ser. No. 08/123175 Lee et al., filed September 1993, Lee et al., PCT U.S. Ser. No. 94/10529 filed Sep. 16, 1994 and Lee et al., Nature 300, n(72), 739–746 (December 1994) whose disclosures are incorporated by reference herein in its entirety describes the above noted method for screening drugs to identify compounds which interact with and bind to the cytokine specific binding protein (hereinafter CSBP). However, for purposes herein the binding protein may be in isolated form in solution, or in immobilized form, or may be genetically engineered to be expressed on the surface of recombinant host cells such as in phage display system or as fusion proteins. Alternatively, whole cells or cytosolic fractions comprising the CSBP may be employed in the screening protocol. Regardless of the form of the binding protein, a plurality of compounds are contacted with the binding protein under conditions sufficient to form a compound/binding protein complex and compound capable of forming, enhancing or interfering with said complexes are detected.

CSBP/p38 Kinase Assay

This assay measures the CSBP/p38-catalyzed transfer of $^{32}P$ from $[a-^{32}P]ATP$ to threonine residue in an epidermal growth factor receptor (EGFR)-derived peptide (T669) with the following sequence: KRELVEPLTPSGEAPNQALLR (residues 661–681). (See Gallagher et al., "Regulation of Stress Induced Cytokine Production by Pyridinyl Imidazoles: Inhibition of CSBP Kinase", BioOrganic & Medicinal Chemistry, 1997, 5, 49–64).

Reactions were carried in round bottom 96 well plate (from Corning) in a 30 ml volume. Reactions contained (in final concentration): 25 mM Hepes, pH 7.5; 8 mM $MgCl_2$; 0.17 mM ATP (the $Km_{[ATP]}$ of p38 (see Lee et al., Nature 300, n72 pg. 639–746 (December 1994)); 2.5 uCi of [g-32P] ATP; 0.2 mM sodium orthovanadate; 1 mM DTT; 0.1% BSA; 10% glycerol; 0.67 mM T669 peptide; and 2–4 nM of yeast-expressed, activated and purified p38. Reactions were initiated by the addition of [gamma-32P]Mg/ATP, and incubated for 25 min. at 37° C. Inhibitors (dissolved in DMSO) were incubated with the reaction mixture on ice for 30 minutes prior to adding the 32P-ATP. Final DMSO concentration was 0.16%. Reactions were terminated by adding 10 ul of 0.3 M phosphoric acid, and phosphorylated peptide was isolated from the reactions by capturing it on p81 phosphocellulose filters. Filters were washed with 75 mM phosphoric acids, and incorporated 32P was quantified using beta scintillation counter. Under these conditions, the specific activity of p38 was 400–450 pmol/pmol enzyme, and the activity was linear for up to 2 hr of incubation. The kinase activity values were obtained after subtracting values generated in the absence of substrate which were 10–15% of total values.

Exemplified compounds herein of Examples 2 to 18, and 20 to 22 have all demonstrated positive inhibitory activity of an $IC_{50}$ of <50 uM in this kinase assay. The compound of Example 19 was not tested.

Prostoglandin Endoperoxide Synthase-2 (PGHS-2) Assay

The following assay describes a method for determining the inhibitory effects of compounds of Formula (I) on human PGHS-2 protein expression in LPS stimulated human monocytes.

Method

Human peripheral blood monocytes were isolated from buffy coats by centrifugation through Ficoll and Percoll gradients. Cells were seeded at $2\times10^6$/well in 24 well plates and allowed to adhere for 1 hour in RPMI supplemented with 1% human AB serum, 20 mM L-glutamine, Penicillin-Streptomycin and 10 mM HEPES. Compounds were added at various concentrations and incubated at 37° C. for 10 minutes. LPS was added at 50 ng/well (to induce enzyme expression) and incubated overnight at 37° C. The supernatant was removed and cells washed once in cold PBS. The cells were lysed in 100 µl of cold lysis buffer(50 mM Tris/HCl pH 7.5, 150 mM NaCl, 1% NP40, 0.5% sodium deoxycholate, 0.1% SDS, 300 ug/ml DNAse, 0.1% TRITON X-100, 1 mM PMSF, 1 mM leupeptin, 1 mM pepstatin). The lysate was centrifuged (10,000×g for 10 min. at 4° C.) to remove debris and the soluble fraction was subjected to SDS PAGE. analysis (12% gel). Protein separated on the gel were transferred onto nitrocellulose membrane by electrophoretic means for 2 hours at 60 volts. The membrane was pretreated for one hour in PBS/0.1% Tween 20 with 5% non-fat dry milk. After washing 3 times in PBS/Tween buffer, the membrane was incubated with a 1:2000 dilution of a mono-specific antiserum to PGHS-2 or a 1:1000 dilution of an antiserum to PGHS-1 in PBS/Tween with 1% BSA for one hour with continuous shaking. The membrane was washed 3× in PBS/Tween and then incubated with a 1:3000 dilution of horseradish peroxidase conjugated donkey antiserum to rabbit Ig (Amersham) in PBS/Tween with 1% BSA for one hour with continuous shaking. The membrane was then washed 3× in PBS/Tween and the ECL immunodetection system (Amersham) was used to detect the level of expression of prostaglandin endoperoxide synthases-2.

Results

The following compounds were tested and found to be active in this assay (i.e., inhibited LPS induced PGHS-2 protein expression in rank order potency similar to that for inhibiting cytokine production as noted in assays indicated): 6-(4-Fluoro-phenyl)-2,3-dihydro-5-(4-pyridinyl)imidazo[2, 1-b]thiazole; and Dexamethasone Several compounds were tested and found to be inactive (up to 10 uM): 2-(4-Methylsulfinylphenyl)-3-(4-pyridyl)-6, 7-dihydro-(5H)-pyrrolo[1,2-a]imidazole; Rolipram; phenidone and NDGA. None of these compounds tested were found to inhibit PGHS-1 or $cPLA_2$ protein levels in similar experiments.

TNF-α in Traumatic Brain Injury Assay

The present assay provides for examination of the expression of tumor necrosis factor mRNA in specific brain regions which follow experimentally induced lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury, n=18). Animals are sacrificed by decapitation at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA is isolated and Northern blot hybridization is performed and quantitated relative to an TNF positive control RNA (macrophage=100%). A marked increase of TNF-α mRNA expression is observed in LH (104±17% of positive control, p<0.05 compared with sham), LC (105±21%, p<0.05) and LA (69±8%, p<0.01) in the traumatized hemisphere 1 hr. following injury. An increased TNF-α mRNA expression is also observed in LH (46±8%, p<0.05), LC (30±3%, p<0.01) and LA (32±3%, p<0.01) at 6 hr. which resolves by 24 hr. following injury. In the contralateral hemisphere, expression of TNF-α mRNA is increased in RH (46±2%, p<0.01), RC (4±3%) and RA (22±8%) at 1 hr. and in RH (28±11%), RC (7±5%) and RA (26±6%, p<0.05) at 6 hr. but not at 24 hr. following injury. In sham (surgery without injury) or naive animals, no consistent changes in expression of TNF-α mRNA is observed in any of the 6 brain areas in either hemisphere at any times. These results indicate that following parasagittal fluid-percussion brain injury, the temporal expression of TNF-α mRNA is altered in specific brain regions, including those of the non-traumatized hemisphere. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma.

CNS Injury Model For IL-β mRNA

This assay characterizes the regional expression of interleukin-1β (IL-1β) mRNA in specific brain regions following experimental lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury). Animals are sacrificed at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (H) and right hippocampus (RH) were prepared. Total RNA is isolated and Northern blot hybridization is performed and the quantity of brain tissue IL-1β mRNA is presented as percent relative radioactivity of IL-1β positive macrophage RNA which is loaded on same gel. At 1 hr. following brain injury, a marked and significant increase in expression of IL-1β mRNA is observed in LC (20.0±0.7% of positive control, n=6, p<0.05 compared with sham animal), LH (24.5±0.9%, p<0.05) and LA (21.5±3.1%, p<0.05) in the injured hemisphere, which remained elevated up to 6 hr. post injury in the LC (4.0±0.4%, n=6, p<0.05) and LH (5.0±1.3%, p<0.05). In sham or naive animals, no expression of IL-1β MRNA is observed in any of the respective brain areas. These results indicate that following TBI, the temporal expression of IL-1β MRNA is regionally stimulated in specific brain regions. These regional changes in cytokines, such as L-1β play a role in the post-traumatic pathologic or regenerative sequelae of brain injury.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C.). Mass spectra were performed upon a VG Zab mass spectrometer using fast atom bombardment, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Flash Chromatography is run over a Merck Silica gel 60 (230–400 mesh).

EXAMPLE 1

Polymer-bound 2-thiopyrimidine-4-carboxaldehyde a) Polymer-bound 2-thiopyrimidine-4-carboxaldehyde Dimethyl Acetal Sodium 2-methylthiopyrimidine-4-carboxaldehyde dimethyl acetal (116 grams (hereinafter 'g"), 560 millimoles (hereinafter "mmol")) was added to a mixture of Merrifield resin (1.4 mmol/g, 100 g, 140 mmol) in DMF (500 milliliter (hereinafter "mL")). After stirring at ambient temperature for about 18 hours (hereinafter "h"), the reaction mixture was filtered and the resin was washed successively with DMF, $CH_2Cl_2$ and MeOH and dried to afford a yellow-colored resin; yield 116 g (94%): MASNMR (CDCl$_3$) δ8.5 (1H, pyrimidine H-6), 5.2 [1H, (MeO)$_2$CH—], 3.3 [6H—((OCH$_3$)$_2$].

b) Polymer-bound 2-thiopyrimidine-4-carboxaldehyde

A mixture of Polymer-bound 2-thiopyrimidine 4carboxaldehyde dimethyl acetal (135 g, 189 mmol maximum) in TFA (150 mL) was heated to reflux for 18 h. The reaction mixture was cooled to ambient temperature and filtered, washed successively with $CH_2Cl_2$ and 5% Et$_3$N in $CH_2Cl_2$ to afford the title material as a orangish-yellow resin; yield 107 g (85%): MASNMR δ9.9 (1H, CHO), 8.6 (1H, pyrimidine H-6).

EXAMPLE 2

1-Cyclohexyl-4-(4-fluorophenyl)-5-[(2-phenylamino) pyrimidin-4-yl]imidazole a) Polymer-bound 2-thiopyrimidine-4carboxaldehyde (cyclohexyl)imine A mixture of Polymer-bound 2-thiopyrimidine-4-carboxaldehyde (5.0 g, 7.0 mmol maximum) and cyclohexylamine (1.6 g, 14 mmol) in $CH_2Cl_2$ (50 mL) were stirred at room temperature for about 18 h. The reaction mixture was filtered and the resin washed with $CH_2Cl_2$ to afford the title material.

b) Polymer-bound 1cyclohexyl-4-(4-fluorophenyl)-5-[(2-thio)pyrimidin-4-yl]imidazole A mixture of the entire sample of polymer-bound 2-thiopyrimidine-4-carboxaldehyde(cyclohexyl)imine from Example 2a (7.0 mmol maximum), 4-fluorophenyl-tolylsulfonomethylisocyanide (6.0 g, 21 mmol), and TBD (2.9 g, 21 mmol), in $CH_2Cl_2$ (50 mL) were stirred at room temperature for 18 h. The reaction mixture was filtered and the resin was washed successively with $CH_2Cl_2$, MeOH and $CH_2Cl_2$ to afford the title material.

c) Polymer-bound 1-cyclohexyl-4-(4-fluorophenyl)-5-[(2-sulfonyl)pyrimidin-4-yl]imidazole A mixture of polymer-bound 1-cyclohexyl-4-(4-fluorophenyl)-5-[(2-thio)pyrimidin-4-yl]imidazole (1.5 g, 2.1 mmol maximum) and 3-peroxybenzoic acid (>95%, 0.54 g, 3.2 mmol) in $CH_2Cl_2$ (30 mL) were stirred at room temperature for 18 h. The reaction mixture was filtered and washed with $CH_2Cl_2$ to afford the title material.

d) 1-Cyclohexyl-4-(4-fluorophenyl)-5-[(2-phenylamino) pyrimidin-4-yl]imidazole

Trimethyl aluminum (2M in tol, 1.0 mL, 2.1 mmol) was added to a suspension of aniline hydrochloride (0.27 g, 2.1 mmol) in toluene (10 mL). The reaction mixture was stirred for 1 h at rt. Polymer-bound 1-cyclohexyl-4-(4-fluorophenyl)-5-[(2-sulfonyl)pyrimidin-4-yl]imidazole (0.50 g, 0.70 mmol maximum) was added and the mixture was heated to 90° C. for 18 h. After cooling to ambient temperature, the reaction mixture was poured into $CH_2Cl_2$ containing silica gel. After bubbling had ceased, the mixture was filtered and the filtrate washed successively with $CH_2Cl_2$, 2% MEOH in $CH_2Cl_2$ and 4% $CH_2Cl_2$. Filtrates containing product were concentrated and the residue was further purified by vacuum filtration through silica eluting successively with 25%, 33% and 50% EtOAc/hexanes to afford the title compound as a chromatographically pure red foam; yield 0.057 g (20% overall). Trituration with ether afforded a light pink solid: ESMS m/z=414 ($M^+$+H).

EXAMPLE 3
1-Cyclohexyl-4-(4-fluorophenyl)-5-[[2[(N-(3-morpholino) propyl]amino]pyrimidin-4-yl]imidazole A mixture of polymer-bound 1-cyclohexyl-4-(4-fluorophenyl)-5-[(2-sulfonyl)pyrimidin-4-yl]imidazole (1.0 g, 1.4 mmol maximum), 4-(3-aminopropyl)morpholine (0.61 mL, 0.60 g, 4.2 mmol) in THF was stirred at room temperature for 18 h. The reaction mixture was filtered and the resin washed with THF. The combined filtrates were concentrated and the residue was vacuum filtered through a pad of silica gel eluting successively with 2% and 4% MeOH in $CH_2Cl_2$. Fractions containing product were concentrated and the residue was triturated with ether to afford the title compound as an off-white solid; yield 0.17 g (26% overall): ESMS m/z=465 ($M^+$+H).

EXAMPLE 4
1-Cyclohexyl-4-(4-fluorophenyl)-5-[[2-[N-(2-imidazol-4-yl)ethyl]amino]pyrimidin-4-yl]imidazole Following the procedure of Example 3 except substituting histamine for 4-(3-aminopropyl)morpholine afforded the title compound as an off-white solid in 14% overall yield: ESMS m/z=432 ($M^+$+H).

EXAMPLE 5
1-Cyclohexyl-4-(fluorophenyl)-5-[[2-[N-(3-pyridyl)methyl] amino]pyrimidin-4-yl]imidazole Following the procedure of Example 3 except substituting 3-aminomethypyridine for 4-(3-aminopropyl)morpholine afforded the title compound as an off-white solid in 10% overall yield: ESMS m/z=429 ($M^+$+H).

EXAMPLE 6
1-Cyclohexyl-4-(4-fluorophenyl)-5-[[2-[N-(3,3-diphenyl) propyl]amino]pyrimidin-4-yl]imidazole Following the procedure of Example 3 except substituting 3,3-diphenylpropylamine for 4-(3-aminopropyl)morpholine afforded the title compound as a white solid in 12% overall yield: ESMS m/z=532 ($M^+$+H).

EXAMPLE 7
(±)-1-Cyclohexyl-4-(-4-fluorophenyl)-5-[[2-[N-(1-methyl-3-phenyl)propyl]amino]pyrimidin-4-yl]imidazole Following the procedure of Example 3 except substituting 1-methyl-3-phenyl propylamine for 4-(3-aminopropyl) morpholine afforded the title compound as a light yellow oil in 17% overall yield: ESMS m/z=532 ($M^+$+H). The free base was dissolved in MeOH and an excess of 3N HCl was added. The solution was concentrated and the residue was subjected to high vacuum and subsequently treated with ether to afford a hygroscopic tan solid.

EXAMPLE 8
N-4-[[[4-(4-Fluorophenyl)]-5-[[2-[(-trifuoromethy)phenyl] amino]]pyrimidine-4-yl]imidazol-4-yl]piperdinyl-N'-[(3-trifluoromethyl)phenyl]urea a) Polymer-bound 2-thiopyrimidine-4-carboxaldehyde[4-amino-1-(ethoxycarbonyl)piperidine]imine Following the procedure of Example 2a except substituting 4-amino-1-(ethoxycarbonyl)-piperidine for cyclohexylamine afforded the title material.

b) Polymer-bound 1-[1-(ethoxycarbonyl)piperdin-4-yl]-4-(4-fluorophenyl)-5-[(2-thio)pyrimidin-4-yl]imidazole Following the procedure of Example 2b except substituting polymer-bound 2-thiopyrimidine-4-carboxaldehyde[4-amino-1-(ethoxycarbonyl)piperidine]imine for polymer-bound 2-thiopyrimidine-4-carboxaldehyde(cyclohexyl)imine afforded the title material.

c) Polymer-bound 1-[1-(ethoxycarbonyl)piperdin-4-yl]4-(4-fluorophenyl)-5-[(2-sulfonyl)pyrimidin-4-yl]imidazole Following the procedure of Example 2c except substituting polymer-bound 1-[1-(ethoxycarbonyl)piperdin-4-yl]-4-(4-fluorophenyl)-5-[(2-thio)pyrimidin-4-yl]imidazole for polymer-bound 1-cyclohexyl-4-(4-fluorophenyl)-5-[(2-thio) pyrimidin-4-yl]imidazole afforded the title material d) N-4-[[[4-(4-Fluorophenyl)]-5-[[2-[(3-trifluoromethyl) phenyl]-amino]]pyrimidine-4-yl]imidazol-4-yl]piperidinyl-N'-[(3-trifluoromethyl)phenyl]urea The reaction was conducted in a manner analogous to Example 2d except substituting polymer-bound 1-[1-ethoxycarbonyl)piperdin-4-yl]-4-(4-fluorophenyl)-5-[(2-sulfonyl)pyrimidin-4-yl]imidazole for polymer-bound 1-cyclohexyl-4-(4-fluorophenyl)-5-[(2-sulfonyl)pyrimidin-4-yl]imidazole except the work-up was modified in the following manner: The cooled reaction mixture was poured into aqueous. NaOH (2.5 N), the layers were separated and the organic phase was washed with 2 times with $H_2O$ and the layers were separated. The organic phase was filtered to remove any remaining resin and the solvents were evaporated under reduced pressure. The residue was purified by vacuum filtration through a pad of silica gel eluting with 2% MEOH in $CH_2Cl_2$. Concentration of fractions containing only product were concentrated and the residue was triturated with ether to afford the title compound as an off-white solid in 26% overall yield: ESMS m/z=670 ($M^+$+H).

EXAMPLE 9
N-[2-[4-(4-fluorophenyl-5-[[2-(3,4-dichlorobenzyl) pyrimidin-4-yl]-1H-imidazol-1-yl]ethyl]-3,4-dimethoxybenzamide a) Polymer-bound 2-thiopyrimidine-4-carboxaldehyde[[[3-(t-butyloxycarbonyl)amino]ethyl]imine Following the procedure of Example 2a except substituting 2-(t-butyloxy-carbonylamino)ethylamine for cyclohexylamine afforded the title material.

b) Polymer-bound 1-[2-(t-butyloxycarbonylamino)ethyl]-4-(4-fluorophenyl)-5-[(2-thio)pyrimidin-4-yl]imidazole Following the procedure of Example 2b except substituting polymer-bound 2-thiopyrimidine-4-carboxaldehyde[[3-(t-butyloxycarbonyl)amino]ethyl]imine for polymer-bound 2-thiopyrimidine-4-carboxaldehyde(cyclohexyl)imine afforded the title material.

c) Polymer-bound 1-(2-aminoethyl)-4-(4-fluorophenyl)-5-[(2-thio)pyrimidin-4-yl]imidazole Polymer-bound 1-[2-(t-butyloxycarbonylamino)ethyl]-4-(4-fluorophenyl)-5-[(2-thio)pyrimidin-4-yl]imidazole was stirred for 18 h at rt. The reaction mixture was filtered and the resin was washed successively with $CH_2Cl_2$ and 5% $Et_3N$ in $CH_2Cl_2$ to afford the title material.

d) Polymer-bound N-[2-[4-(4-fluorophenyl)-5-[2-4thio)pyrimidin-4-yl]-1H-imidazol-1-yl]ethyl]-3,4-dimethoxybenzamide 3,4-Dimethoxybenzoyl chloride (2.7 g, 13 mmol) was added to a mixture of polymer-bound 1-(2-aminoethyl)-4-(4-fluorophenyl)-5-[(2-thio)pyrimidin-4-yl]imidazole (1.9 g, 2.7 mmol maximum), $Et_3N$ (1.8 mL, 1.3 g, 13 mmol) in $CH_2Cl_2$ (100 mL). The reaction mixture was stirred for 18 h, filtered and washed successively with $CH_2Cl_2$, MeOH and $CH_2Cl_2$ to afford the title material.

e) Polymer-bound N[2-[4-(4-fluorophenyl)-5-[2-(sulfonyl)pyrimidin-4-yl]-1H-imidazol-1-yl]ethyl]-3,4-dimethoxybenzamide Following the procedure of Example 2c except substituting polymer-bound N-[2-[4-(4-fluorophenyl)-5-[2-(thio)pyrimidin-4-yl]-1H-imidazol-1-yl]ethyl]-3,4-dimethoxybenzamide for polymer-bound 1-cyclohexyl-4-(4-fluorophenyl)-5-[(2-thio)pyrimidin-4-yl]imidazole afforded the title material.

f) N[2-[4-(4-fluorophenyl-5-[[2-(3,4-dichlorobenzyl)pyrimidin-4-yl]-1H-imidazol-1-yl]ethyl]-3,4-dimethoxybenzamide 3,4-Dichlorobenzylamine (0.36 mL, 0.48 g, 2.7 mmol) was added to a mixture of polymer-bound N-[2-[4-(4-fluorophenyl)-5-[2-(sulfonyl)pyrimidin-4-yl]-1H-imidazol-1-yl]ethyl]-3,4-dimethoxybenzamide in toluene (15 mL). The reaction mixture was heated to 90° C. for 18 h. Polymer-bound 2-thiopyrimidine-4-carboxaldehyde (1.9 g, 2.7 mmol) was added and the mixture was stirred for an additional 4 h to remove excess 3,4-dichlorobenzylamine. The reaction mixture was poured directly through a pad of silica gel eluting successively with 1%, 2% and 4% MeOH in $CH_2Cl_2$. Fractions containing product were combined and the solvent evaporated. The residue was triturated with ether to afford an off-white solid; yield 0.045 g (8% overall): ESMS m/z=622 ($M^++H$).

EXAMPLE 10
N-[2-[4-(4-Fluorophenyl)-5-[[2-(4-methoxybenzylamino)pyrimidin-4-yl]-1H-imidazol-1-yl]ethyl]-ethoxyacetamide a) Polymer-bound N-[2-[4-(4-fluorophenyl)-5-[2-(thio)pyrimidin-4-yl]-1H-imidazol-1-yl]ethyl]-ethoxyacetamide Following the procedure of Example 9d except substituting methoxyacetyl chloride for 3,4-dimethoxybenzoyl chloride afforded the title material.

b) Polymer-bound N[2-[4-(4-fluorophenyl)-5-[2-(sulfonyl)pyrimidin-4-yl]-1H-imidazol-1-yl]ethyl]-ethoxyacetamide Following the procedure of Example 2c except substituting polymer-bound N[2-[4-(4-fluorophenyl)-5-[2-(thio)pyrimidin-4-yl]-1H-imidazol-1-yl]ethyl]ethoxyacetamide for polymer-bound 1-cyclohexyl-4-(4-fluorophenyl)-5-[(2-thio)pyrimidin-4-yl]imidazole afforded the title material.

c) N-[2-[4-(4-Fluorophenyl)-5-[[2-(4-methoxybenzylamino)pyrimidin-4-yl]-1H-imidazol-1-yl]ethyl]-ethoxyacetamide Following the procedure of Example 9f except substituting 4-methoxybenzylamine for 3,4-dichlorobenzylamine and polymer-bound N-[2-[4-(4-fluorophenyl)-5-[2-(sulfonyl)pyrimidin-4-yl]-1H-imidazol-1-yl]ethyl] ethoxyacetamide for polymer-bound N-[2-[4-(4-fluorophenyl)-5-[2-(sulfonyl)pyrimidin-4-yl]-1H-imidazol-1-yl]ethyl]-3,4-dimethoxybenzamide afforded the title material in 24% yield: ESMS m/z=491 ($M^++H$).

EXAMPLE 11
1-Isopropyl-4-(4-fluorophenyl)-5-[2-phenylamino-pyrimidin-4yl]imidazole a) Polymer-bound 2-thiopynmidine-4-carboxaldehyde isopropyl)imine Following the procedure of Example 2a except substituting isopropylamine for cyclohexylamine afforded the title material.

b) Polymer-bound 1-isopropyl-4-(4-fluorophenyl)-5-[(2-thio)pyrimidin-4-yl]imidazole Following the procedure of Example 2b except substituting polymer-bound 2-thiopyrimidine-4-carboxaldehyde (isopropyl)imine for polymer-bound 2-thiopyrimidine-4-carboxaldehyde(cyclohexyl)imine afforded the title material.

c) Polymer-bound 1-isopropyl-4-(4-fluorophenyl)-5-[(2-sulfonyl)pyrimidin-4yl]imidazole Following the procedure of Example 2c except substituting polymer-bound 1-isopropyl-4-fluorophenyl)-5-[(2-thio)pyrimidin-4-yl]imidazole for polymer-bound 1-cyclohexyl-4(4-fluorophenyl)-5-[(2-thio)pyrimidin-4-yl]imidazole afforded the title material d) 1-Isopropyl-4-(4-fluorophenyl-5-[2-phenylamino-pyrimidin-4-yl]imidazole The reaction was conducted in a manner analogous to Example 2d except substituting polymer-bound 1-isopropyl-4-(4-fluorophenyl)-5-[(2-sulfonyl)pyrimidin-4-yl]imidazole for polymer-bound 1-cyclohexyl-4-(4-fluorophenyl)-5-[(2-sulfonyl)pyrimidin-4-yl]imidazole: ESMS m/z=374 (MH)$^+$

EXAMPLE 12
1-Cyclopentyl-4-(4-fluorophenyl)-5-[2-phenylamino-pyrimidin-4yl]imidazole a) Polymer-bound 2-thiopyrimidine-4-carboxaldehyde (cyclopentyl)imine Following the procedure of Example 2a except substituting cyclopentylamine for cyclohexylamine afforded the title material.

b) Polymer-bound 1-cyclopentyl-4(4-fluorophenyl)-5-[(2-thiopyrimidin-4-yl]imidazole Following the procedure of Example 2b except substituting polymer-bound 2-thiopyrimidine-4-carboxaldehyde (cyclopentyl)imine for polymer-bound 2-thiopyrimidine-4-carboxaldehyde(cyclohexyl)imine afforded the title material.

c) Polymer-bound 1-cyclopentyl-4-(4-fluorophenyl)-5-[(2-sulfonyl)pyridin-4-yl]imidazole Following the procedure of Example 2c except substituting polymer-bound 1-cyclopentyl-4-(4-fluorophenyl)-5-[(2-thio)pyrimidin-4-yl]imidazole for polymer-bound 1-cyclohexyl-4-(4-fluorophenyl)-5-[(2-thio)pyrimidin-4-yl] imidazole afforded the title material d) 1-Cyclopentyl-4-(4-fluorophenyl)-5-[2-phenylamino-pyrimidin-4-yl]imidazole The reaction was conducted in a manner analogous to Example 2d except substituting polymer-bound 1-cyclopentyl-4-(4-fluorophenyl 5-[(2-sulfonyl)pyrimidin-4-yl]imidazole for polymer-bound 1-cyclohexyl-4-(4-fluorophenyl)-5-[(2-sulfonyl)pyrimidin-4yl]imidazole: ESMS m/z=400 (MH)$^+$

EXAMPLE 13
a) 1-[(1-t-butoxycarbonyl)-4-piperidinyl]-4-(4-fluorophenyl)-5-[2-methyl-4-fluorophenyl)amino]pyrimidin-4-yl]imidazole Trimethylaluminum (2M in toluene, 2.9 mL, 5.8 mmol) was added to a stirred solution of 2-methyl-4-fluoroaniline (0.483 g, 3.5 mmol) in toluene (8 mL) at ambient temperature. Stirring was continued until gas evolution ceased (~1 h) and 1-[(1-t-butoxycarbonyl)-4-piperidinyl]-4-(fluorophenyl)-5-{2-methysulfinylpyrimidin-4-yl]imidazole (0.485 g, 1.0 mmol) was added. The resulting solution was stirred for 2 h at 230 and poured into a slurry of silica gel in $CH_2Cl_2$. The solids were removed by filtration and washed with 10% MeOH in $CH_2Cl_2$. The combined filtrates were concentrated and the residue was purified by flash chromatography eluting with 0–2% MeOH in $CH_2Cl_2$ to afford the title compound as a white solid: yield 0.452 g (82%): ESMS m/z=547 ($M^+$+H).

b) 1-(4-piperidinyl)-4-(4-fluorophenyl)-5-[2-(2-methyl-4-fluorophenyl)amino]pyrimidin-4-yl]imidazole The product of the preceding example (285 mg, 0.52 mmol) and TFA (10 mL) were combined at 23°, stirred 40 min. and the resulting yellow solution was concentrated. The residue was dissolved in EtOAc (75 mL) and washed with 10% aqueous NaOH, dried ($Na_2SO_4$) and concentrated to ca 10 mL. Crystals formed on standing and slow cooling to 4°. Filtration afforded 187 mg (80%). ESP+MS m/z 447($MH^+$).

EXAMPLE 14

1-(4-Piperidinyl)-4-(4-fluorophenyl)-5-[2-(2-methyl-5-fluorophenyl)amino]pyrimidin-4-yl]imidazole Following the procedure of example 13 except using 2-methyl-5-fluoro-aniline the title compound was obtained as a white solid. ESP+MS m/z 447($MH^+$).

EXAMPLE 15

1-(4-Piperdinyl)-4-(4-fluorophenyl)-5-[2-(2,6-dimethylphenyl)amino]pyrimidin-4-yl]imidazole Following the procedure of example 13 except using 2,6-dimethyl aniline the title compound was obtained as a white solid. ESP+MS m/z 443($MH^+$).

EXAMPLE 16

1-(4-Piperidinyl)-4-(4-fluorophenyl)-5-[2-(2-methylphenyl)amino]pyrimidin-4-yl]imidazole Following the procedure of example 13 except using 2-methylaniline the title compound was obtained as a white solid. ESP+MS m/z 429($M^+$).

Using analogous procedures to those indicated above, the following compounds have also been synthesized:

EXAMPLE 17

1-(4-Fluorophenyl)-4-(4-fluorophenyl)-5-[2-phenylamino-pyrimidin-4-yl]imidazole; MS ES+=426 (MH+)

EXAMPLE 18

1-(4-Fluorophenyl)-4-(4-fluorophenyl)-5-[2-(4-fluorophenylamino)pyrimidin-4-yl]imidazole; MS ES+=444 (MH+)

EXAMPLE 19

1-(4-Fluorophenyl)-4-(4-fluorophenyl)-5-[2-(4-methylphenylamino)pyrimidin-4-yl]imidazole; MS ES+=440 (MH+)

EXAMPLE 20

1-(4-Fluorophenyl)-4-(4-fluorophenyl)-5-[2-(2-methylphenylamino)pyrimidin-4-yl]imidazole; MS ES+=440 (MH+)

EXAMPLE 21

1-(4-Fluorophenyl)-4-(4-fluorophenyl)-5-[2-(2,6-dimethylphenylamino)pyrimidin-4-yl]imidazol; MS ES+=454 (MH+)

EXAMPLE 22

1-(4-Fluorophenyl)-4-(4-fluorophenyl)-5-[2-(4-2-morpholinylphenylamino)-pyrimidin-4-yl]imidazole MS ES+=511 (MH+)

EXAMPLE 23

Using an alternative method of synthesis the compound of Example 16 was also produced:
1-(4-Piperidinyl)-4-(4-Fluorophenyl)-5-[(2-methylphenyl)amino]pyrimidin-4-yl]imidazole a) 2-Propylthiopyrimidine-4-carboxaldehyde Dimethyl Acetal Charge a 1 Liter (hereinafter "L") 3-necked flask equipped with a stir bar, thermometer, 100 mL addition funnel and reflux condenser with N,N-dimethylformamide dimethyl acetal (88.7 g, 98.9 mL, 700 mmol) and pyruvaldehyde dimethyl acetal (85.3 g, 86.8 mL, 700 mmol) and heat in an oil bath at 1100 for about 3 to 4 hours. Cool the solution to 85° and add thiourea (48.9 g, 636.4 mmol) and NaOMe (25 wt % in MeOH, 151.2 g, 160 mL, 700 mmol) and stir at 85° for about 3 to 4 h. Cool the solution to 65° and charge 1-bromoropane (86.9 g, 64.4 mL, 700 mmol) to the addition funnel and add slowly over 10–15 min to the reaction, bringing the solution to a mild reflux. After 1 h, add 100 mL of EtOAC to the reaction and bring the oil bath temperature to 95°. Replace the reflux condenser with a distillation head and distill 150–200 mL of solvent from the reaction. Add an additional 400 mL of EtOAc and 120 mL of $H_2O$ and stir at 50° about 5 minutes. Transfer to a separatory funnel and separate the aqueous phase. Add 60 mL of $H_2O$, agitate, and separate the aqueous phase. A sample was concentrated to give a yellow oil: 1H NMR (300 MHz, $CDCl_3$) d 8.53 (1H, d, J 5.0 Hz), 7.16 (1H, d, J=5.0 Hz), 5.17 (1H, s), 3.42 (3H, s), 3.14 (2H, t, J=7.3 Hz), 1.76 (2H, m), 1.05 (3H, t, J=7.3 Hz).

b) 2-Propylthiopyrimidine-4-carboxaldehyde

The product of example 1(a) (10.0 g, 50 mmol), and 3 N HCl (42 mL, 126 mmol) were combined and stirred at 48° C. for 16h, cooled to 23° C., combined with EtOAc (200 mL) and made basic by the addition of solid $Na_2CO_3$ (12.6 g, 150 mmol). The aqueous phase was extracted with EtOAc (4×150 mL, dried ($Na_2SO_4$), concentrated and the residue was filtered through a pad of silica (ca 150 mL) with $CH_2Cl_2$ to afford 7.49 g (97%) of the title compound 1H NMR (400 MHz, $CDCl_3$): δ9.95 (s, 1H), 8.78 (d, 1H), 7.45 (d, 1H), 3.21 (t, 2H), 1.82 (m, 2H), 1.1 (t, 3H).

c) 1-t-Butoxycarbonyl-4-aminopiperidine 1-t-Butoxycarbonyl piperidine-4-one (commercially available from Lancaster Chem) (39.9 g, 0.20 mol), TEF (150 mL), $H_{2O}$ (300 mL), and $H_2NOH$ HCl (55.2, 0.80 mol) were dissolved together and $Na_2CO_3$ (55.2 g, 0.53 mol) was added in small portions. The mixture was stirred at 23° C. for 14 h, most of the TBF was evaporated in vacuo, adjusted to pH>10 with 50% aq NaOH, extracted with EtOAc(5×50 mL) and concentrated to a white foam. Triturated with hexane, filtered and the solid was dried in vacuo to afford 40.31 g.

The above residue was dissolved in EtOH (abs) (1 L) and Raney Ni (50 mL of a slurry in EtOH) was added and the mixture was reduced under $H_2$ (50 psi) for 3.5 h. The catalyst was filtered off and washed with EtOH to afford. Concentration afforded 38.4 g (96% overall) of the title compound as a colorless oil which solidified to a white solid upon standing at −20° C.

d) 2-Propylthiopynmidine-4-carboxaldehyde [1-t-butoxycarbonyl-4-aminopiperidine]imine The product of the previous step (6.72 g, 33.6 mmol), $MgSO_4$ (ca. 5 g), the product of example 1(b) (5.31 g, 29.2 mmol), and $CH_2Cl_2$ (30 mL) were combined and stirred at 23° C. for 16 h. Filtration and concentration of the filtrate afforded the title compound as a yellow oil. $^1H$ NMR ($CDCl_3$): d 8.56 (d, 1), 8.26 (s, 1), 7.57 (d, 1), 4.05 (m, 2), 3.52 (m, 1), 3.18 (t, 2H), 3.00 (m, 2), 1.75 (m, 7), 1.48 (s, 9) 1.05 (t, 3H).

e) 4-Fluorophenyl-tolylsulfonomethylformamide

To a suspension of p-toluenesulfinic acid sodium salt (30 g) in H$_2$O (100 mL) was added methyl t-butyl ether (50 mL) followed by dropwise addition of conc HCl (15 mL). After stirring 5 min, the organic phase was removed and the aqueous phase was extracted with methyl t-butyl ether. The organic phase was dried (Na$_2$SO$_4$) and concentrated to near dryness. Hexane was added and the resulting precipitate collected to afford p-toluenesulfinic acid; yield 22 g.

p-Toluenesulfinic acid (22 g, 140.6 mmol), p-fluorobenzaldehyde (22 mL, 206 mmol), formamide (20 mL, 503 mmol) and camphor sulphonic acid (4 g, 17.3 mmol) were combined and stirred at 60° C. 18 h. The resulting solid was broken up and stirred with a mixture of MeOH (35 mL) and hexane (82 mL) then filtered. The solid was resuspended in MeOH/hexanes (1:3, 200 mL) and stirred vigorously to break up the remaining chunks. Filtration afforded the title compound (27 g, 62% yield): $^1$H NMR (400 MHz, CDCl$_3$) d 8.13 (s, 1H), 7.71 (d, 2H), 7.43 (dd, 2H), 7.32 (d, 2H), 7.08 (t, 2H), 6.34 (d, 1H), 2.45 (s, 3H).

f) 4-Fluorophenyl-tolylsulfonomethylisocyanide

4-Fluorophenyl-tolylsulfonomethylformamide (2.01 g, 6.25 mmol) in DME (32 mL) was cooled to −10° C. POCl$_3$ (1.52 mL, 16.3 mmol) was added followed by the dropwise addition of triethylamine (4.6 mL, 32.6 mmol) in DME (3 mL) keeping the internal temperature below −5° C. The mixture was gradually warned to ambient temperature over 1 h, poured into H$_2$O and extracted with EtOAc. The organic phase was washed with sat aq NaHCO$_3$, dried (Na$_2$SO$_4$), and concentrated. The resulting residue was triturated with petroleum ether and filtered to afford the title compound (1.7 g, 90% yield): $^1$H NMR (CDCl$_3$) d 7.63 (d, 2H), 7.33 (m, 4H), 7.10 (t, 2H), 5.60 (s, 1H), 2.50 (s, 3H).

g) 1-[(1-t-Butoxycarbonyl)piperidin-4-yl]-4-(4-fluorophenyl)-5-[(2-proplthio(pyrimidin-4-yl)]imidazole The product of example 1(d) and the product of the previous example (9.41 g, 32.6 mmol), DMF (64 mL) and K$_2$CO$_3$ (4.43 g, 32.4 mmol) were combined and stirred for 2 days, diluted with Et$_2$O and filtered. The solid was washed with Et$_2$O and the filtrate was concentrated to a yellow solid. Trituration of the solid with Et$_2$O, filtration and washing with more Et$_2$O and drying in vacuo afforded 9.07 g of the title compound as a white solid (62% from the product of example 1(b)). MS ES+m/z=498 (MH$^+$).

h) 1-[(1-t-Butoxycarbonyl)piperidin-4-yl]-4-(4-fluorophenyl-5-[(2-propylsulfinyl)pyrimidin-4-yl)]imidazole The product of the previous example (9.07 g, 19.3 mmol), dissolved in THF (250 mL) was cooled to −10° C. and OXONE (14.2 g, 23.2 mmol) in H$_2$O (250 mL) was added dropwise (T<10°). The resulting mixture was stirred at 23° C. for 1 h, combined with ice (100 mL) and CH$_2$Cl$_2$ (700 mL) shaken and the aqueous was separated. The organic phase was washed with brine (100 mL), dried (Na$_2$SO$_4$), concentrated and dried in vacuo to afford 8.27 g (84%) of the title compound as a white foam. MS ES+m/z=514 (MH$^+$).

i) 1-[(1-t-Butoxycarbonyl)piperidin-4-yl]-4-(4-Fluorophenyl)-5-[(2-methylphenyl)amino]pyrimidin-4-yl]imidazole o-Toluidine (0.19 mL, 175 mmol) and toluene (4 mL) were dissolved together, cooled to 4° and treated dropwise with tri-methylaluminum in toluene (2M) (0.875 mL, 1.75 mmol), stirred 1.5 h at 23° and then the product of the previous step (243 mg, 0.5 mmol) was added in one portion. Stirred 1.5 h and diluted with EtOAc and washed with 10% aq NaOH (2×), dried (Na$_2$SO$_4$), concentrated and the residue was flash chromatographed over silica with 0–2% MEOH in CH$_2$Cl$_2$) to afford 250 mg (95%) of a white foam. MS ES+=529 (MH+).

i) 1-(4-Piperidinyl)-4-(4-Fluorophenyl)-5-[(2-methylphenyl)amino]pyrimidin-4-yl]imidazole The product of the previous step (249 mg, 0.47 mmol) was combined with TFA (10 mL) and the resulting solution was stirred for 15 min, the TFA was evaporated in vacuo, the residue was dissolved in EtOAc, washed with 10% aq NaOH, dried (Na$_2$SO$_4$), concentrated and crystallized from EtOAc and hexane (1:1) to afford 84 mg (42%) of white crystals. MS ES+=429 (MH+).

EXAMPLE 24

Using an alternative method of synthesis the compound of Example 13 was also produced:
1-(4-Piperidinyl)-4-(4-Fluorophenyl)-5-[2-methyl-4-fluorophenyl)amino]pyrimidin-4-yl]imidazole The title compound was prepared by the procedure of example 23 except that 2-methyl-4-fluoroaniline was use as the aniline reactant. MS ES+=447 (MH+).

EXAMPLE 25

Using an alternative method of synthesis the compound of Example 15 was also produced:
1-(4-Piperidinyl)-4-(Fluorophenyl)-5-[2,6-dimethylphenyl)amino]pyrimidin-4-yl]imidazole The title compound was prepared by the procedure of example 23 except that 2,6-dimethylaniline was use as the aniline reactant. MS ES+=443 (MH+).

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows:

What is claimed is:

1. A process of making a compound of Formula (A):

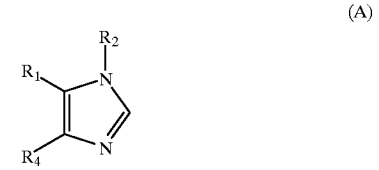

(A)

R$_1$ is 4-pyrimidinyl ring which ring is substituted with NHR$_a$ and optionally substituted with an additional, independent, substituent of C$_{1-4}$ alkyl, halogen, hydroxyl, C$_{1-4}$ alkoxy, C$_{1-4}$ alkylthio, C$_{1-4}$ alkylsulfinyl, CH$_2$OR$_{12}$, amino, mono and di-C$_{1-6}$ alkyl substituted amino, N(R$_{10}$)C(O)R$_b$ or NHR$_a$;

R$_a$ is hydrogen, alky, optionally substituted alkyl, aryl, arylC$_{1-6}$alkyl, heterocyclic, heterocyclylC$_{1-6}$ alky, heteroaryl, or heteroaryl$C_{1-6}$alkyl, wherein each of the aryl, heterocyclic and heteroaryl containing moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_{m'}R_3, OR_3$, halo-substituted-$C_{1-4}$ alkyl, $C_{1-4}$ alkyl, $(CR_{10}R_{20})_{m''}NR_{10}C(Z)R_3$, $NR_{10}S(O)_{m'}R_8$, $NR_{10}S(O)_{m'}NR_7R_{17}$, $ZC(Z)R_3$ or $(CR_{10}R_{20})_{m''}NR_{13}R_{14}$;

v is 0, or an integer having a value of 1 or 2;

m is 0, or the integer 1 or 2;

m' is an integer having a value of 1 or 2, m'' is 0, or an integer having a value of 1 to 5;

$R_2$ is —$(CR_{10}R_{20})_{n'}OR_9$, heterocyclyl, heterocyclyl$C_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$cycloalkenyl-$C_{1-10}$-alkyl, aryl, aryl$C_{1-10}$ alkyl, heteroaryl, heteroaryl-$C_{1-10}$-alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_{n'}SO_2R_{18}$, $(CR_{10}R_{20})_nS(O)_{m'}NR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the aryl, arylalkyl, heteroaryl, heteroaryl alkyl, cycloalkyl, cycloalkyl alkyl, heterocyclic and heterocyclic alkyl groups may be optionally substituted;

n is an integer having a value of 1 to 10;

n' is 0, or an integer having a value of 1 to 10;

Z is oxygen or sulfur, $R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$_{1-4}$alkyl, heterocyclyl, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; wherein the aryl, arylalkyl, heteroaryl, heteroaryl alkyl may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is $R_{10}$ or $C(Z)$—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$_{1-10}$alkyl, heterocyclyl, heterocyclyl-$C_{1-10}$alkyl, heteroaryl or heteroaryl$_{1-10}$alkyl;

$R_{19}$ is hydrogen, cyano, $C_{1-4}$ alkyl, $C_{3-7}$ cycloalkyl or aryl; or a pharmaceutically acceptable salt thereof; which process comprises a) reacting polymer bound 2-thiopyrimidine-4-yl imine of the formula:

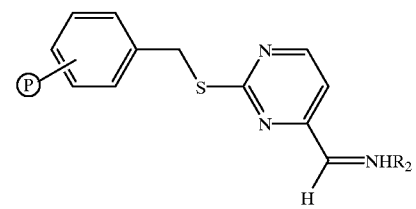

wherein $R_2$ is as defined in Formula (A) above, and P is a polymer solid support; with an isonitrile of the formula:

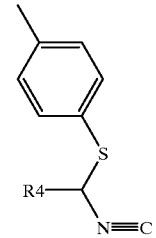

wherein $R_4$ is as defined for Formula (A) above, to yield a polymer-bound 2-thiopyrimidinyl-imidazole of the formula:

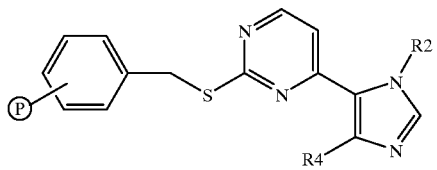

b) wherein the polymer-bound 2-thiopyrimidinyl-imidazole of step (a) is release from the polymer by oxidizing the sulfur moiety to the corresponding sulfone or sulfoxide, or a combinations thereof, of the formula:

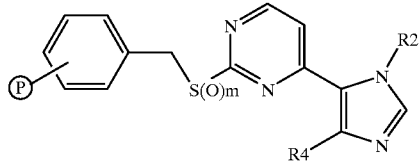

wherein m is 1 or 2; and
c) reacting the sulfone or sulfoxide with an amine of the formula $NH_2R_a$, wherein $R_a$ is as defined in Formula (A), to yield a compound of Formula (A):

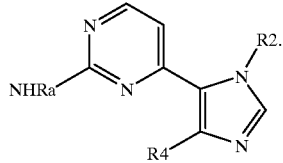

2. The process according to claim 1 wherein the oxidation of the imidazole to the corresponding sulfoxide or sulfone is by reaction with an organic soluble oxidant, 3-chloroperoxybenzoic acid.

3. The process according to claim 1 wherein the oxidation takes place in a solvent which swells the resin.

4. The process according to claim 2 wherein the cycloaddition reaction of the imine with the isonitrile is in an organic solvent which swells the polymer resin, and includes a base which is soluble in this organic solvent.

5. The process according to claim 1 wherein the polymer bound 2-thiopyrimidine-4-yl imine is formed by reaction of a polymer-bound aldehyde of the formula:

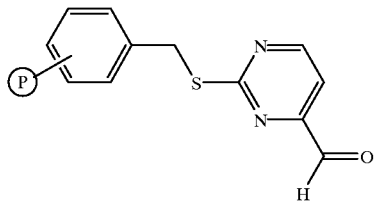

with $NH_2R_2$, wherein $R_2$ is as defined in formula (A).

6. The process according to claim 1 wherein the polymer bound aldehyde is formed by hydrolysis of a polymer-bound pyrimidine acetal of the formula:

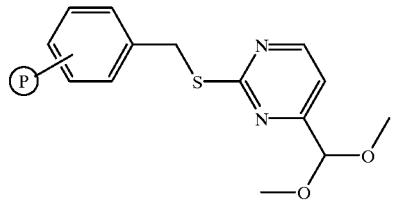

with a strong acid.

7. The process according to claim 6 wherein the acetal is bound to the polymer resin by reaction of a salt form of 2-thiopyrimidine-4-carboxaldehyde with a suitable resin in an organic solvent which swells the resin and dissolves the salt.

* * * * *